United States Patent
Masuda et al.

(10) Patent No.: US 10,172,671 B2
(45) Date of Patent: Jan. 8, 2019

(54) GRASPING TREATMENT DEVICE

(71) Applicant: OLYMPUS CORPORATION, Hachioji-shi, Tokyo (JP)

(72) Inventors: Shinya Masuda, Hino (JP); Ryu Onuma, Tama (JP); Genri Inagaki, Maple Grove, MN (US)

(73) Assignee: OLYMPUS CORPORATION, Tokyo (JP)

( * ) Notice: Subject to any disclaimer, the term of this patent is extended or adjusted under 35 U.S.C. 154(b) by 608 days.

(21) Appl. No.: 14/722,806

(22) Filed: May 27, 2015

(65) Prior Publication Data
US 2015/0282874 A1    Oct. 8, 2015

Related U.S. Application Data

(63) Continuation of application No. 14/078,124, filed on Nov. 12, 2013, which is a continuation of application No. PCT/JP2013/057713, filed on Mar. 18, 2013.

(Continued)

(51) Int. Cl.
*A61B 18/14* (2006.01)
*A61N 7/00* (2006.01)
(Continued)

(52) U.S. Cl.
CPC .. *A61B 18/1445* (2013.01); *A61B 17/320092* (2013.01); *A61N 7/00* (2013.01);
(Continued)

(58) Field of Classification Search
CPC ....... A61B 2017/320093; A61B 2017/320094; A61B 2017/320095; A61B 2017/320082; A61B 17/320092
See application file for complete search history.

(56) References Cited

U.S. PATENT DOCUMENTS 6,340,352 B1    1/2002   Okada et al.
6,558,376 B2    5/2003   Bishop
(Continued)

FOREIGN PATENT DOCUMENTS

CN    101569548 A    11/2009
CN    102292045 A    12/2011
(Continued)

OTHER PUBLICATIONS

Sep. 9, 2014 Office Action issued in Japanese Application No. 2014-116989.

(Continued)

*Primary Examiner* — Jaymi Della
(74) *Attorney, Agent, or Firm* — Oliff PLC

(57) ABSTRACT

A grasping treatment device includes a first electrode portion provided at least one of in a part between a jaw and a probe electric conducting portion in opening-and-closing directions of the jaw and in the probe electric conducting portion, and a second electrode portion provided at least one of in a part between the jaw and the first electrode portion in the opening-and-closing directions of the jaw and in a jaw electric conducting portion. The grasping treatment device includes an inter-electrode distance changing unit changing an inter-electrode distance so that a second distance between the electrode portions in a second treatment mode, in which the high-frequency current alone is transmitted to the first electrode portion and second electrode portion, is smaller than a first distance between the electrode portions in a first treatment mode, in which at least an ultrasonic vibration is transmitted to a probe electric conducting portion.

7 Claims, 24 Drawing Sheets

Related U.S. Application Data

(60) Provisional application No. 61/612,603, filed on Mar. 19, 2012.

(51) Int. Cl.
   *A61B 17/32* (2006.01)
   *A61B 18/00* (2006.01)
   *A61B 17/29* (2006.01)

(52) U.S. Cl.
   CPC ............ *A61B 17/320068* (2013.01); *A61B 2017/2929* (2013.01); *A61B 2018/00607* (2013.01); *A61B 2018/00994* (2013.01)

(56) References Cited

U.S. PATENT DOCUMENTS

| | | | |
|---|---|---|---|
| 2005/0021027 A1* | 1/2005 | Shields | A61B 18/1445 606/51 |
| 2008/0132887 A1 | 6/2008 | Masuda et al. | |
| 2009/0088668 A1 | 4/2009 | Masuda | |
| 2009/0270853 A1 | 10/2009 | Yachi et al. | |
| 2010/0145335 A1* | 6/2010 | Johnson | A61B 18/1445 606/51 |
| 2010/0185196 A1 | 7/2010 | Sakao et al. | |
| 2010/0324458 A1 | 12/2010 | Okada et al. | |
| 2010/0331742 A1* | 12/2010 | Masuda | A61B 17/32009 601/2 |
| 2012/0101493 A1 | 4/2012 | Masuda et al. | |
| 2012/0289957 A1* | 11/2012 | Emmerich | A61B 18/1445 606/41 |

FOREIGN PATENT DOCUMENTS

| | | |
|---|---|---|
| JP | 2004-033565 A | 2/2004 |
| JP | 2010-264260 A | 11/2010 |
| JP | 2011-235147 A | 11/2011 |
| JP | 4856290 B2 | 1/2012 |
| WO | 2005/122918 A1 | 12/2005 |
| WO | 2011/089769 A1 | 7/2011 |

OTHER PUBLICATIONS

Apr. 8, 2014 Office Action issued in Japanese Application No. 2013-545575.
Mar. 18, 2013 International Preliminary Report on Patentability issued in International Patent Application No. PCT/JP2013/057713.
Apr. 16, 2013 International Search Report issued in Application No. PCT/JP2013/057713.
Jan. 10, 2017 Office Action issued in Chinese Patent Application No. 201510409503.9.

* cited by examiner

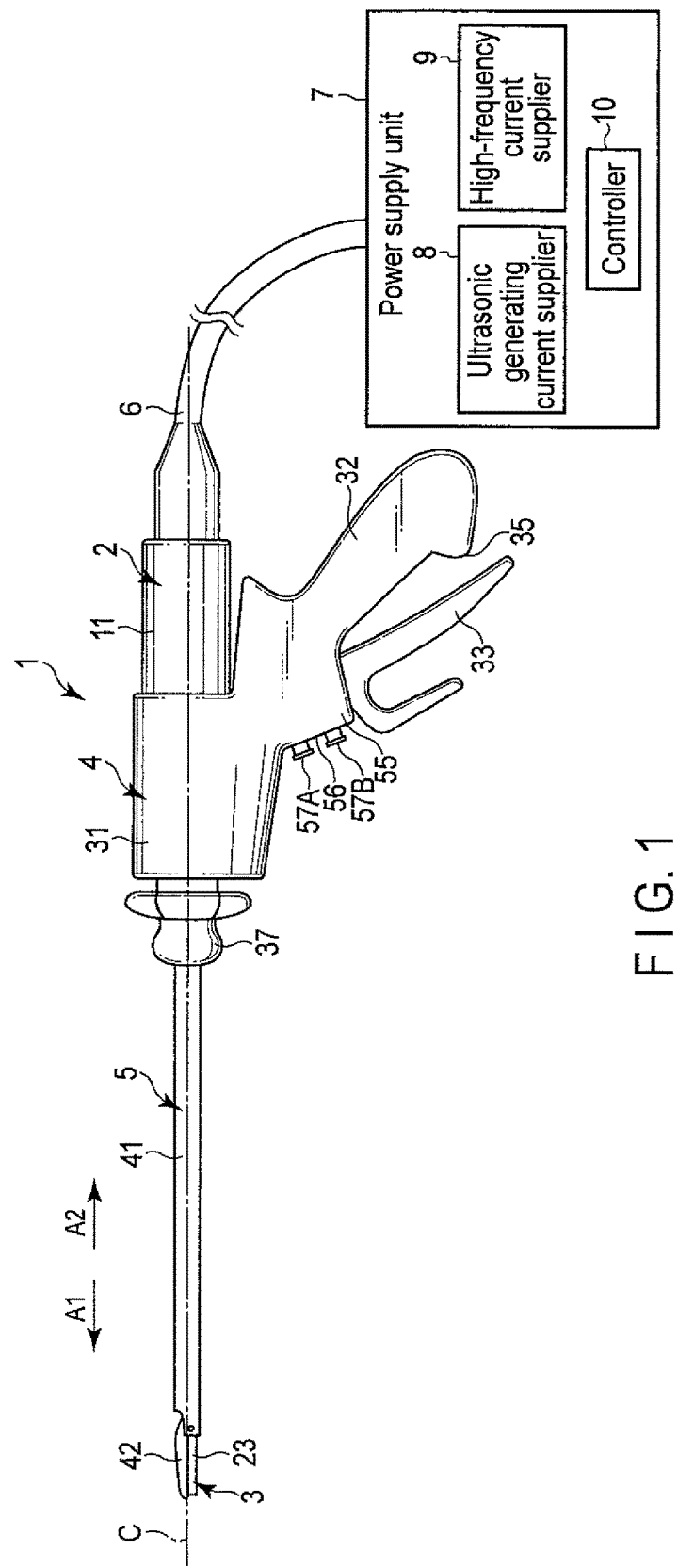
F I G. 1

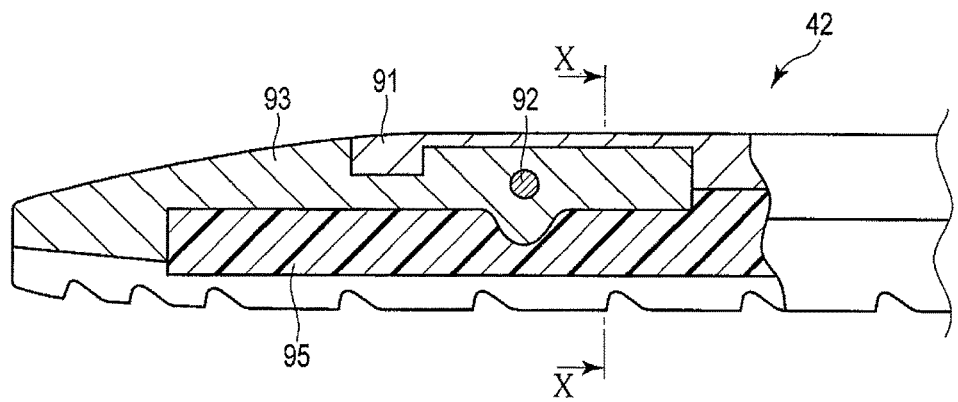
F I G. 9
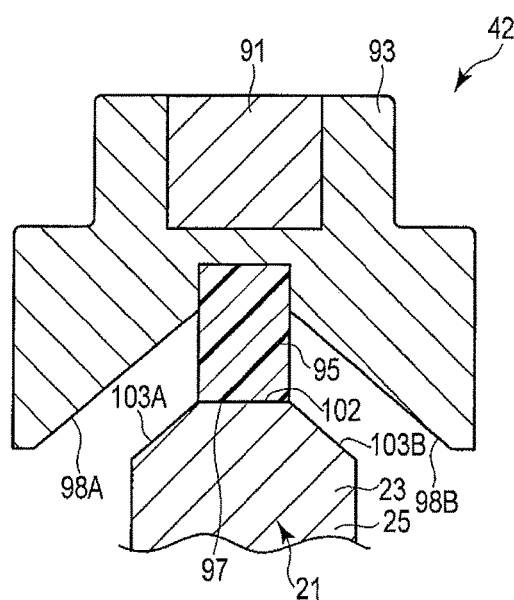
F I G. 10

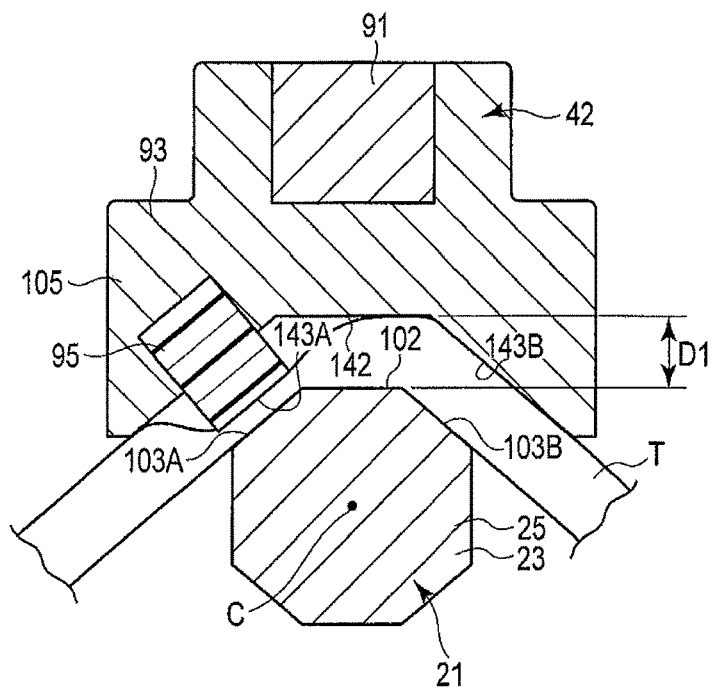
F I G. 19
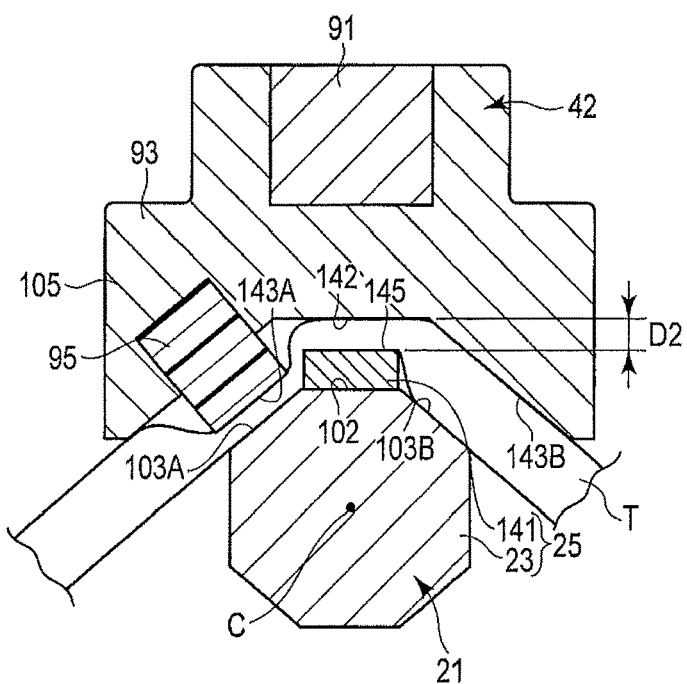
F I G. 20

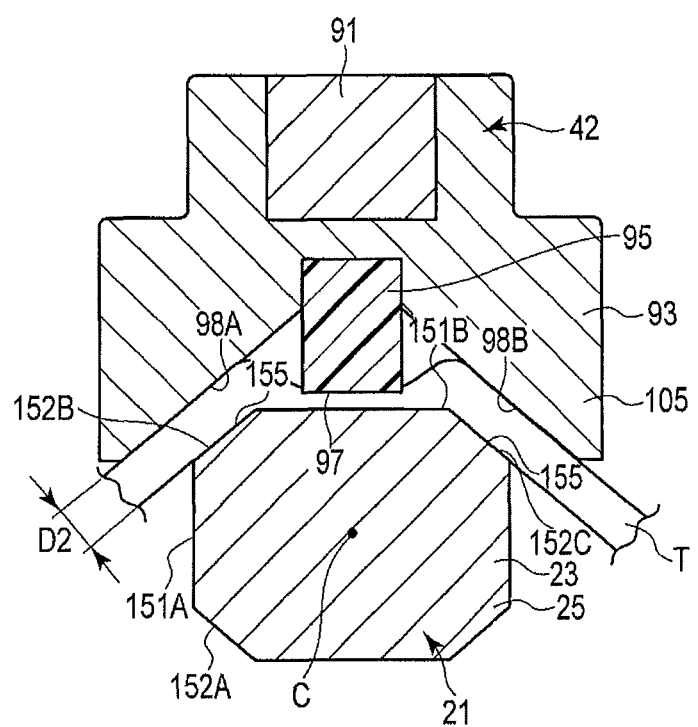
F I G. 25

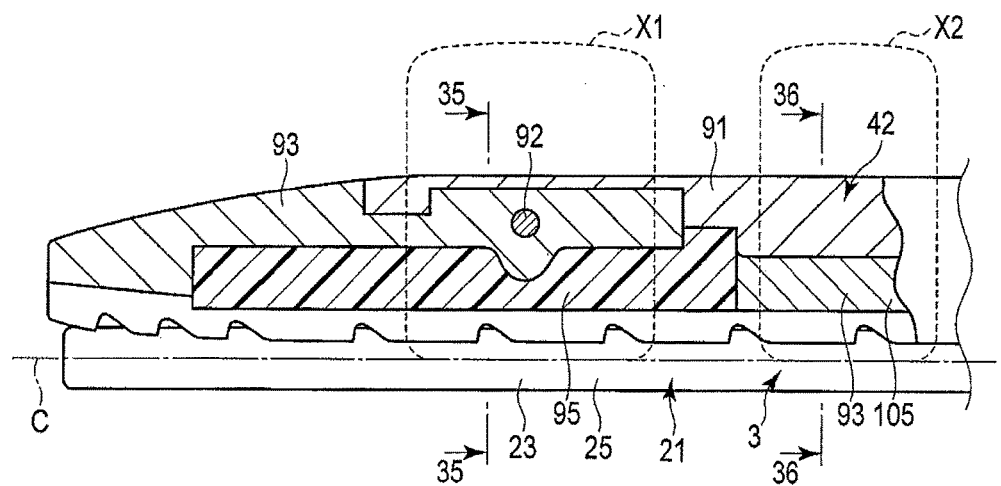
F I G. 34
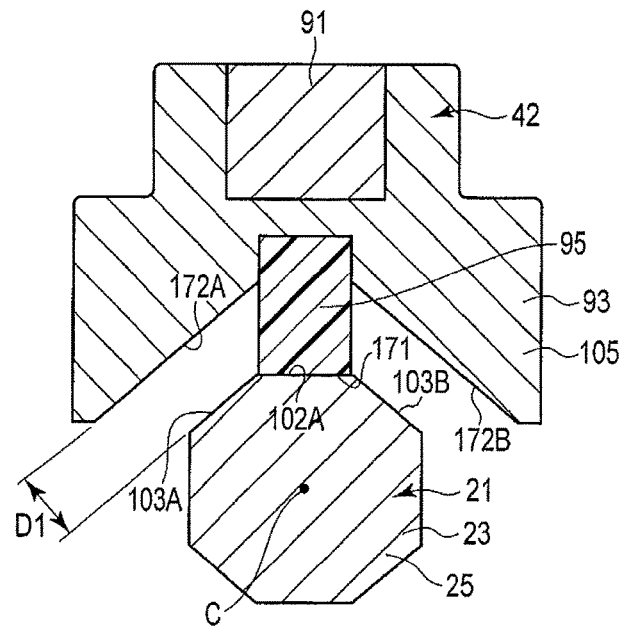
F I G. 35

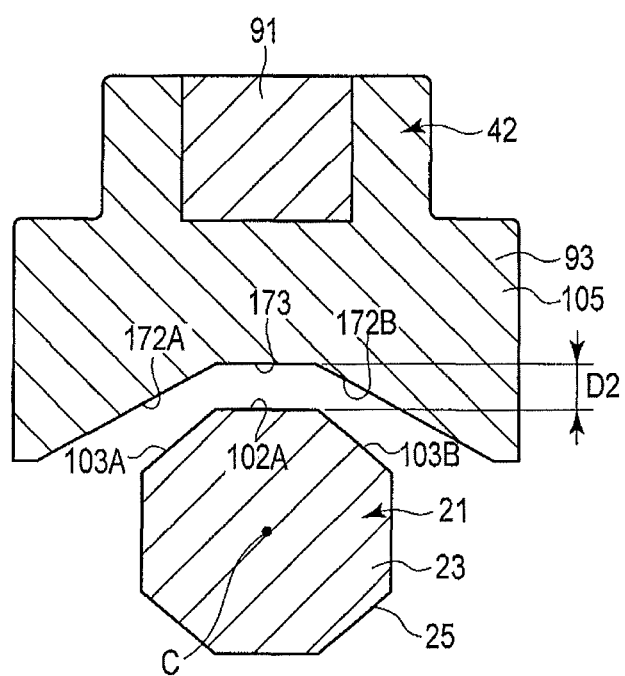
F I G. 36

GRASPING TREATMENT DEVICE

CROSS REFERENCE TO RELATED APPLICATION

This application is a continuation of U.S. application Ser. No. 14/078,124, filed Nov. 12, 2013, the contents of which are incorporated herein by reference.

BACKGROUND OF THE INVENTION

1. Field of the Invention

The present invention relates to a grasping treatment device which is configured to grasp a grasping target such as a living tissue between a distal portion of a probe unit and a jaw configured to open or close relative to the distal portion of the probe unit, and which is configured to treat the grasping target by using, for example, an ultrasonic vibration and a high-frequency current.

2. Description of the Related Art

US 2009/0270853, US 2009/0088668, and US 2008/132887 each disclose a grasping treatment device which includes a probe unit including a first electrode portion (probe electric conducting portion) provided in its distal portion, and a jaw configured to open or close relative to the first electrode portion. In each of the grasping treatment devices, the probe unit includes a probe body which is configured to transmit an ultrasonic vibration from a proximal direction to a distal direction, and the ultrasonic vibration is transmitted to the first electrode portion. A high-frequency current is transmitted to the portion. A high-frequency current is transmitted to the first electrode portion of the probe unit through the probe unit. The probe unit is inserted through a sheath body, and the probe unit is electrically insulated from the sheath body. The jaw is attached to a distal portion of the sheath body. The jaw includes an abutting portion configured to abut on the first electrode portion when the jaw is closed relative to the first electrode portion, and a second electrode portion having a clearance between the first electrode portion and the second electrode portion when the abutting portion is in abutment with the first electrode portion. The abutting portion of the jaw is made of an insulating material. A high-frequency current is transmitted to the second electrode portion through the sheath body.

In a first treatment mode which is one treatment mode, the ultrasonic vibration is transmitted to the first electrode portion (the distal portion of the probe unit) when a living tissue such as a blood vessel is grasped between the first electrode portion and the jaw. At the same time, a high-frequency current is transmitted to the first electrode portion and the second electrode portion. The probe unit is ultrasonically vibrated while the grasping target such as living tissue is grasped between the distal portion of the probe unit and the jaw, and frictional heat is thereby generated between the distal portion of the probe unit and the living tissue. The living tissue is simultaneously cut and coagulated between the distal portion of the probe unit and the jaw by the generated frictional heat. At the same time, a high-frequency current runs through the living tissue grasped between the first electrode portion and the second electrode portion. The living tissue is reformed by the high-frequency current, and the coagulation of the living tissue is accelerated. In a second treatment mode different from the first treatment mode, a high-frequency current alone is transmitted to the first electrode portion and the second electrode portion while a living tissue such as a blood vessel is grasped between the first electrode portion and the jaw. At this time, a high-frequency current runs through the living tissue grasped between the first electrode portion and the second electrode portion, and the living tissue is only coagulated.

BRIEF SUMMARY OF THE INVENTION

According to one aspect of the invention, a grasping treatment device includes that: a probe unit including a probe body which extends along a longitudinal axis and which is configured to transmit an ultrasonic vibration from a proximal direction toward a distal direction, the probe body including a probe electric conducting portion in its distal portion; a sheath unit including a sheath body through which the probe unit is inserted, the sheath unit being electrically insulated from the probe unit; a jaw attached to a distal portion of the sheath unit to be openable and closable relative to the probe electric conducting portion, the jaw including an abutting portion which is made of an insulating material and which is be abutable on the probe electric conducting portion when the jaw is closed relative to the probe electric conducting portion, and a jaw electric conducting portion which is configured to form a clearance between the jaw electric conducting portion and the probe electric conducting portion when the abutting portion is in abutment with the probe electric conducting portion; a first electrode portion which is provided at least one of in a part between the jaw and the probe electric conducting portion in opening-and-closing directions of the jaw and in the probe electric conducting portion, the first electrode portion having a first electric potential when a high-frequency current is transmitted thereto through the probe unit; a second electrode portion which is provided at least one of in the part between the jaw and the first electrode portion in the opening-and-closing directions of the jaw and in the jaw electric conducting portion, the second electrode portion having a second electric potential different in intensity from the first electric potential when a high-frequency current is transmitted thereto through the sheath unit; and an inter-electrode distance changing unit configured to change an inter-electrode distance so that a second distance between the first electrode portion and the second electrode portion in a second treatment mode, in which the high-frequency current alone is transmitted to the first electrode portion and the second electrode portion, is smaller than a first distance between the first electrode portion and the second electrode portion in a first treatment mode, in which at least the ultrasonic vibration is transmitted to the probe electric conducting portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing a grasping treatment device according to a first embodiment of the present invention;

FIG. 9 is a partly sectional schematic side view showing the jaw according to the first embodiment;

FIG. 10 is a sectional view taken along the line X-X in FIG. 9;

FIG. 19 is a schematic sectional view showing configurations of a distal portion of a probe unit, a distal portion of a sheath unit, and a jaw according to a second embodiment of the present invention in the first treatment mode;

FIG. 20 is a schematic sectional view showing the configurations of the distal portion of the probe unit, the distal portion of the sheath unit, and the jaw according to the second embodiment in the second treatment mode;

FIG. 25 is a schematic sectional view showing the configurations of the distal portion of the probe unit and the jaw according to the third embodiment in the second treatment mode;

FIG. 34 is a partly sectional schematic side view showing a distal portion of a probe unit and a jaw according to a reference example of the present invention;

FIG. 35 is a sectional view taken along the line 35-35 in FIG. 34; and

FIG. 36 is a sectional view taken along the line 36-36 in FIG. 34.

Figure 2:
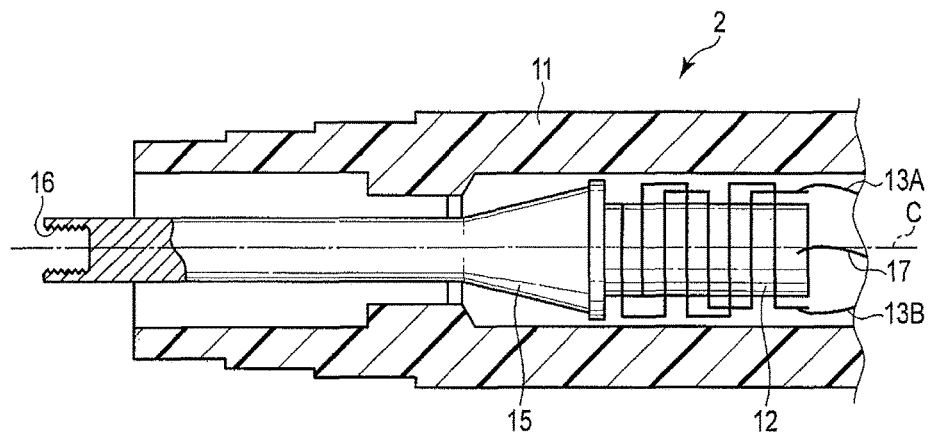
FIG. 2 is a schematic sectional view showing the configuration of a vibrator unit (oscillator unit) according to the first embodiment.

DETAILED DESCRIPTION OF THE INVENTION (First Embodiment)

A first embodiment of the present invention is described with reference to FIG. 1 to FIG. 15. FIG. 1 is a schematic view showing a grasping treatment device 1 according to the present embodiment. As shown in FIG. 1, the grasping treatment device 1 has a longitudinal axis C. Here, one of two directions parallel to the longitudinal axis C is a distal direction (direction of an arrow A1 in FIG. 1), and a direction opposite to the distal direction is a proximal direction (direction of an arrow A2 in FIG.

The grasping treatment device 1 which is a surgical treatment device includes a vibrator unit (oscillator unit) 2, a probe unit 3, a handle unit 4, and a sheath unit 5. The vibrator unit 2 includes a vibrator case (oscillator case) 11. One end of a cable 6 is connected to a proximal end of the vibrator case 11. The other end of the cable 6 is connected to a power supply unit 7. The power supply unit 7 includes an ultrasonic generating current supplier 8, a high-frequency current supplier 9, and a controller 10. The grasping treatment device 1 and the power supply unit 7 constitute a surgical treatment system.

FIG. 2 is a diagram showing a configuration of the vibrator unit 2. As shown in FIG. 2, an ultrasonic vibrator (ultrasonic oscillator) 12 including a piezoelectric element configured to convert a current to an ultrasonic vibration is provided in (inside) the vibrator case 11. One end of each of electric signal lines 13A and 13B is connected to the ultrasonic vibrator 12. Each of the electric signal lines 13A and 13B has the other end connected to the ultrasonic generating current supplier 8 of the power supply unit 7 through an inside of the cable 6. The ultrasonic vibration is generated in the ultrasonic vibrator 12 by the supply of a current to the ultrasonic vibrator 12 from the ultrasonic generating current supplier 8 via the electric signal lines 13A and 13B. A columnar horn 15 configured to increase the amplitude of the ultrasonic vibration is coupled to the distal direction side of the ultrasonic vibrator 12.

The horn 15 is supported by the vibrator case 11, and is electrically insulated from the vibrator case 11. An internal thread 16 is formed in a distal portion of the horn 15. In addition to the electric signal lines 13A and 13B, an electric signal line 17 which extends from the high-frequency current supplier 9 of the power supply unit 7 through the inside of the cable 6 is connected to the ultrasonic vibrator 12.

Figure 3:
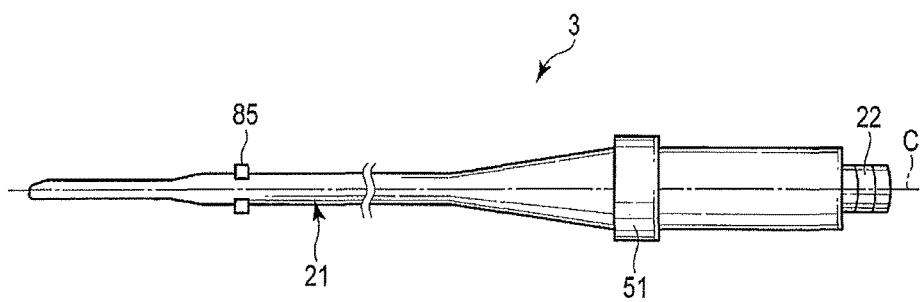
FIG. 3 is a schematic side view showing the configuration of a probe unit according to the first embodiment.

FIG. 3 is a diagram showing the configuration of the probe unit 3. As shown in FIG. 3, the probe unit 3 includes a columnar probe body 21 extending along the longitudinal axis C. The longitudinal axis C of the grasping treatment device 1 passes through an axial center of the probe body 21. An external thread 22 is provided in a proximal-direction-side portion of the probe body 21. When the external thread 22 of the probe body 21 is screwed to the internal thread 16 of the horn 15, the probe body 21 (the probe unit 3) is attached to the horn 15.

When the probe body 21 is attached to the horn 15, the ultrasonic vibration generated in the ultrasonic vibrator 12 can be transmitted to a distal portion of the probe body 21 (the probe unit 3) via the horn 15. That is, the probe body 21 can transmit the ultrasonic vibration from the proximal direction to the distal direction. A probe electric conducting portion 23 is provided in the distal portion of the probe body 21 (the probe unit 3). When the probe body 21 is attached to the horn 15, a high-frequency current can be transmitted to the probe electric conducting portion 23 from the high-frequency current supplier 9 through the electric signal line 17, the ultrasonic vibrator 12, the horn 15, and the probe body 21 (the probe unit 3). When the high-frequency current is transmitted, the probe electric conducting portion 23 functions as a first electrode portion 25 having a first electric potential E1.

As shown in FIG. 1, the handle unit 4 includes a cylindrical case 31 extending along the longitudinal axis C. The cylindrical case 31 is made of an insulating material. A fixed handle 32 extends from the cylindrical case 31 in a direction tilted relative to the longitudinal axis C. The fixed handle 32 is formed integrally with the cylindrical case 31. A movable handle 33 is rotatably (pivotably) attached to the cylindrical case 31. The movable handle 33 is configured to open or close relative to the fixed handle 32 substantially parallel to the longitudinal axis C. The movable handle 33 is located to the distal direction side of the fixed handle 32. A stopper 35 is provided on a distal-direction-side surface of the fixed handle 32. When the movable handle 33 abuts on the stopper 35, the movement of the movable handle 33 relative to the fixed handle 32 toward (in) a closing direction is regulated.

The vibrator unit 2 is coupled to the cylindrical case 31 from the proximal direction side, and the sheath unit 5 is coupled to the cylindrical case 31 from the s distal direction side. The probe unit 3 is inserted into the cylindrical case 31 from the distal direction side. The sheath unit 5 includes a cylindrical sheath body 41 through which the probe unit 3 is inserted. A jaw 42 is rotatably (pivotably) attached to a distal portion of the sheath body 41. The jaw 42 is configured to open or close relative to the probe electric conducting portion 23 (the first electrode portion 25) of the probe body 21.

The handle unit 4 also includes a rotational operation knob 37 which is a rotational operation input portion coupled to the distal direction side of the cylindrical case 31. The rotational operation knob 37 is coupled to the cylindrical case 31 rotatably in directions around the longitudinal axis. When the rotational operation knob 37 rotates relative to the cylindrical case 31, the vibrator unit 2, the probe unit 3, the sheath unit 5, and the jaw 42 rotate relative to the cylindrical case 31 in one of the directions around the longitudinal axis.

Figure 4:
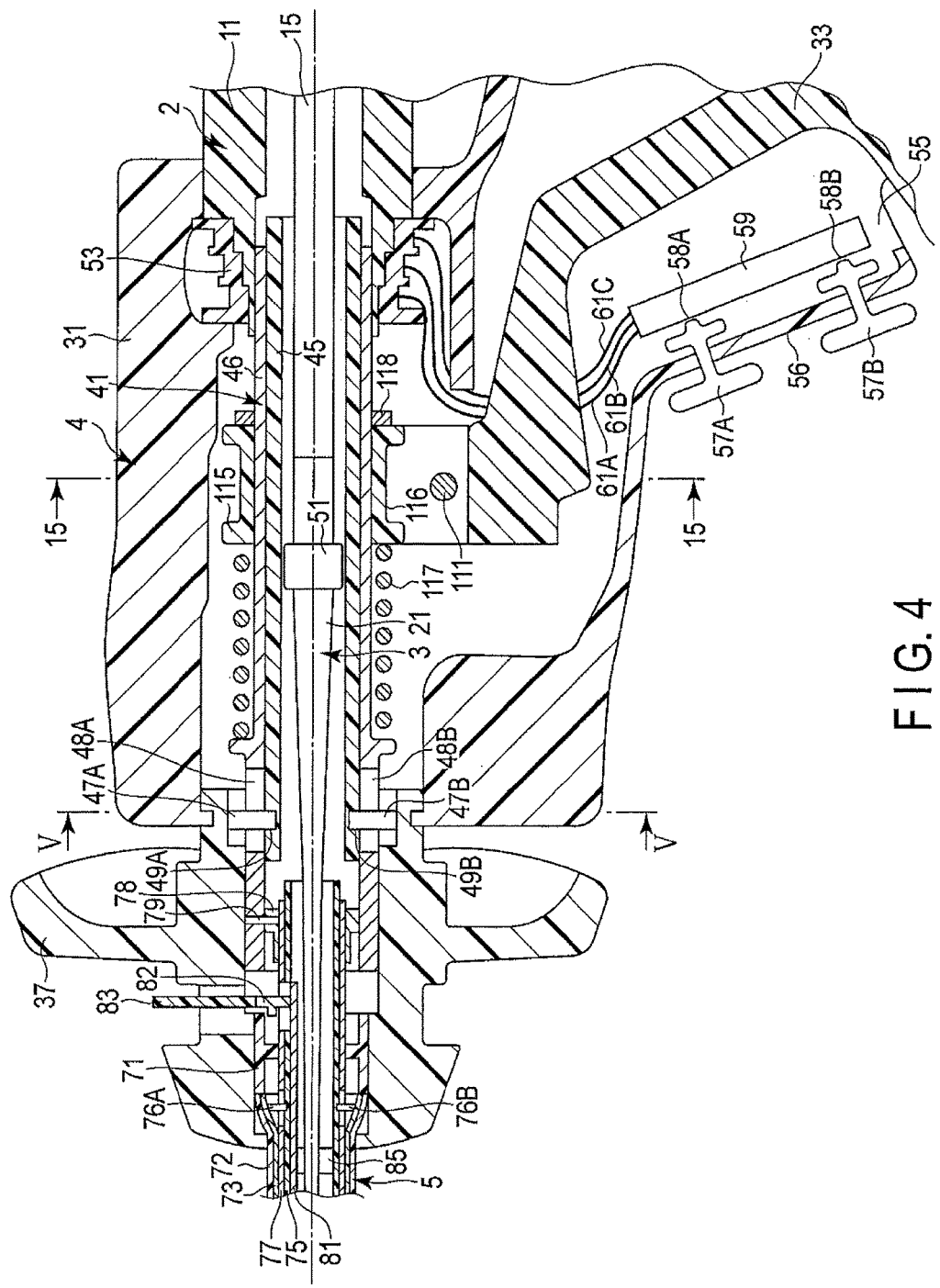
FIG. 4 is a schematic sectional view showing an internal configuration of a handle unit according to the first embodiment.

FIG. 4 is a diagram showing an internal configuration of the handle unit 4. As shown in FIG. 4, the probe body 21 (the probe unit 3) and the sheath body 41 (the sheath unit 5) extend up to the inside of the cylindrical case 31 along the longitudinal axis C through an inside of the rotational operation knob 37. The proximal end of the probe body 21 is attached to the horn 15 inside the cylindrical case 31. As a result, the vibrator unit 2 is coupled to the probe unit 3. A proximal portion of the sheath body 41 is coupled to the vibrator case 11 inside the cylindrical case 31. As a result, the vibrator unit 2 is coupled to the sheath unit 5.

A connection cylindrical member 45 which couples the probe body 21 to the sheath body 41 is provided inside the cylindrical case 31 of the handle unit 4. The sheath body 41 includes a movable cylindrical member 46 provided to an outer peripheral direction side of the connection cylindrical member 45. The connection cylindrical member 45 and the movable cylindrical member 46 are provided along the longitudinal axis C. The connection cylindrical member 45 is made of an insulating material such as a resin. The movable cylindrical member 46 is made of an electrically conducting material such as a metal.

Figure 5:
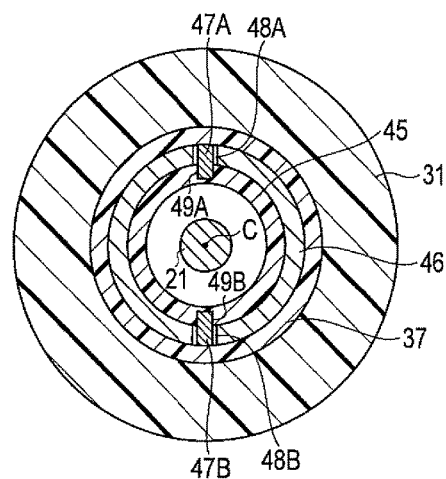
FIG. 5 is a sectional view taken along the line V-V in FIG. 4.

FIG. 5 is a sectional view taken along the line V-V in FIG. 4. As shown in FIG. 4 and FIG. 5, engaging pins 47A and 47B are fixed to the rotational operation knob 37 so that these engaging pins 47A and 47B are located apart from each other in the directions around the longitudinal axis. The engaging pins 47A and 47B protrude toward an inner peripheral direction from an inner peripheral portion of the rotational operation knob 37. Through-holes 48A and 48B are provided in the movable cylindrical member 46 so that these through-holes 48A and 48B are located apart from each other in the directions around the longitudinal axis. Each of the through-holes 48A and 48B is formed into the shape of a long hole along the longitudinal axis C, and diametrically passes through the movable cylindrical member 46. The connection cylindrical member 45 is provided with engaging depressions 49A and 49B that are depressed toward the inner peripheral direction. The engaging depressions 49A and 49B are provided apart from each other in the directions around the longitudinal axis.

The engaging pin 47A is inserted through the through-hole 48A, and is engaged with the engaging depression 49A. The engaging pin 47B is inserted through the through-hole 48B, and is engaged with the engaging depression 49B. When each of the engaging pins 47A and 47B is engaged with the corresponding engaging depression 49A or 49B, the connection cylindrical member 45 is fixed to the rotational operation knob 37. When each of the engaging pins 47A and 47B is inserted through the corresponding through-hole 48A or 48B, the movable cylindrical member 46 and the rotational operation knob 37 are regulated unrotatably relative to each other in the directions around the longitudinal axis. However, as each of the through-holes 48A and 48B is formed into the shape of a long hole along the longitudinal axis C, the movable cylindrical member 46 is movable relative to the rotational operation knob 37 and the connection cylindrical member 45 along the longitudinal axis C. According to the configuration described above, the connection cylindrical member 45 and the movable cylindrical member 46 are rotatable relative to the cylindrical case 31 together with the rotational operation knob 37 in the directions around the longitudinal axis. Moreover, the movable cylindrical member 46 is movable relative to the probe body 21 (the probe unit 3) and the handle unit 4 along the longitudinal axis C.

An elastic member 51 made of an insulating material is fixed to an outer peripheral portion of a proximal portion of the probe body 21 (see FIG. 3). When the probe body 21 is coupled to the horn 15, the elastic member 51 is located at a node position of the ultrasonic vibration. The elastic member 51 is pressed toward the inner peripheral direction by an inner peripheral portion of the connection cylindrical member 45, and is contracted. The probe body 21 (the probe unit 3) is fixed to the connection cylindrical member 45 by the contraction of the elastic member 51. As a result, the probe body 21 (the probe unit 3) is coupled to the sheath body 41 (the sheath unit 5) by the connection cylindrical member 45 and the elastic member 51.

When the rotational operation knob 37 is rotated in the directions around the longitudinal axis, a rotational drive force from the rotational operation knob 37 is transmitted to the probe body 21 (the probe unit 3) via the connection cylindrical member 45 and the elastic member 51. Consequently, the probe unit 3 can rotate relative to the cylindrical case 31 together with the rotational operation knob 37 and the connection cylindrical member 45. Since the connection cylindrical member 45 and the elastic member 51 are made of an insulating material, the probe body 21 (the probe unit 3) is electrically insulated from the movable cylindrical member 46.

As shown in FIG. 4, the movable cylindrical member 46 and the vibrator case 11 are engaged with each other so that the movable cylindrical member 46 is inserted into the vibrator case 11 in a coupling portion of the sheath body 41 (the sheath unit 5) and the vibrator case 11 (the vibrator unit 2). The rotation of the movable cylindrical member 46 and the vibrator case 11 relative to each other in the directions around the longitudinal axis is regulated. However, the movable cylindrical member 46 is movable relative to the vibrator case 11 along the longitudinal axis C.

An electric connection ring 53 is provided to the outer peripheral direction side of the vibrator case 11 in a coupling portion of the sheath body 41 and the vibrator case 11. The electric connection ring 53 is provided so that the electric connection ring 53 is fixed to the cylindrical case 31 of the handle unit 4. When the vibrator case 11 is coupled to the sheath body 41 (movable cylindrical member 46), an outer peripheral portion of a distal portion of the vibrator case 11 is in contact with the electric connection ring 53, and an inner peripheral portion of a distal portion of the vibrator case 11 is in contact with the movable cylindrical member 46. The vibrator case 11 and the sheath body 41 are rotatable together relative to the electric connection ring 53 in the directions around the longitudinal axis.

A switch arrangement portion 55 is provided between the cylindrical case 31 and the fixed handle 32. The switch arrangement portion 55 is formed integrally with the cylindrical case 31 and the fixed handle 32. The switch arrangement portion 55 includes a flat portion 56 substantially perpendicular to the longitudinal axis C. The flat portion 56 is provided on the side where the fixed handle 32 and the movable handle 33 are located with the longitudinal axis C being a center. The flat portion 56 is located to the distal direction side of the movable handle 33.

Treatment mode input buttons 57A and 57B which are treatment mode input portions are provided on the flat portion 56. When each of the treatment mode input buttons 57A and 57B is pressed, an input operation of switching to a treatment mode selected by a surgeon is performed. Switch portions 58A and 58B, and an electric circuit substrate 59 are provided in (inside) the switch arrangement portion 55. The switch portion 58A is turned on or off by the input operation in the treatment mode input button 57A. Similarly, the switch portion 58B is turned on or off by the input operation in the treatment mode input button 57B.

Figure 6:
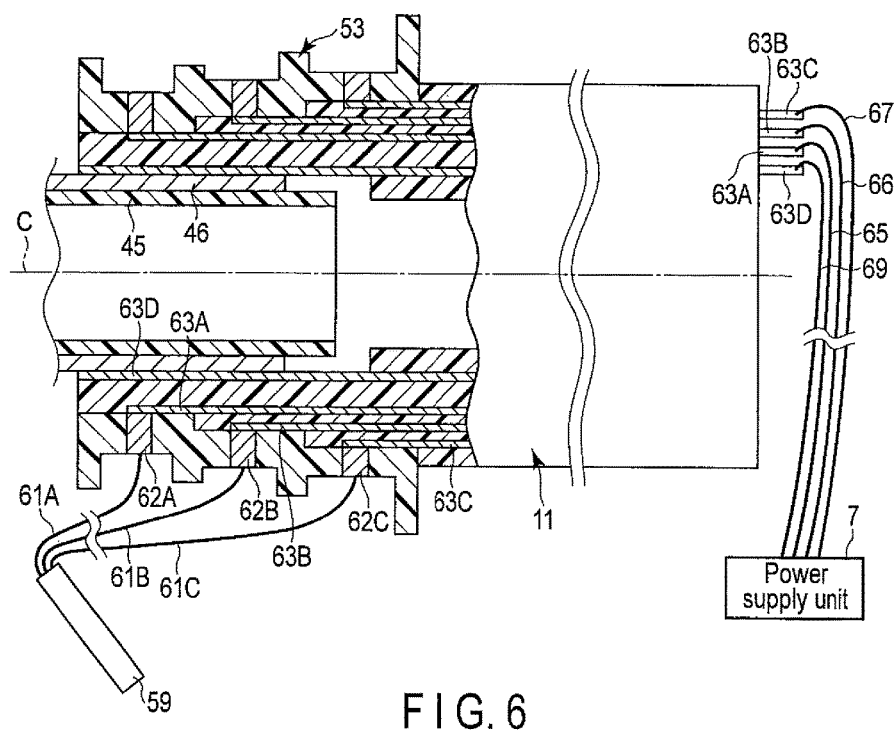
FIG. 6 is a schematic view showing an electric connection state in a vibrator case according to the first embodiment.

FIG. 6 is a schematic view showing an electric connection state in the vibrator case 11. As shown in FIG. 4 and FIG. 6, three electric signal lines, 61A to 61C, are provided in the cylindrical case 31. The electric signal line 61A is electrically connected to the switch portion 58A via an electric circuit on the electric circuit substrate 59. The electric signal line 61B is electrically connected to the switch portion 58B via the electric circuit on the electric circuit substrate 59. The electric signal line 61C is electrically connected to the switch portion 58A and the switch portion 58B via the electric circuit on the electric circuit substrate 59. The electric signal line 61C is a common line shared as a ground line of the switch portion 58A and the switch portion 58B.

The electric connection ring 53 includes a first electric connection portion 62A, a second electric connection portion 62B, and a third electric connection portion 62C. The first electric connection portion 62A is electrically insulated from the second electric connection portion 62B. The second electric connection portion 62B is electrically insulated from the third electric connection portion 62C. The first electric connection portion 62A is electrically insulated from the third electric connection portion 62C. The electric signal line 61A is connected to the first electric connection portion 62A. The electric signal line 61B is connected to the second electric connection portion 62B. The electric signal line 61C is connected to the third electric connection portion 62C.

The vibrator case 11 includes a first electric conducting portion 63A, a second electric conducting portion 63B, and a third electric conducting portion 63C. The first electric conducting portion 63A, the second electric conducting portion 63B, and the third electric conducting portion 63C extend along the longitudinal axis C. The first electric conducting portion 63A is electrically insulated from the second electric conducting portion 63B. The second electric conducting portion 63B is electrically insulated from the third electric conducting portion 63C. The first electric conducting portion 63A is electrically insulated from the third electric conducting portion 63C. When the vibrator case 11 is coupled to the movable cylindrical member 46 (the sheath body 41), a distal portion of the first electric conducting portion 63A alone is in electric contact with the first electric connection portion 62A of the electric connection ring 53. Similarly, a distal portion of the second electric conducting portion 63B alone is in electric contact with the second electric connection portion 62B of the electric connection ring 53. A distal portion of the third electric conducting portion 63C alone is in electric contact with the third electric connection portion 62C of the electric connection ring 53.

One end of an electric signal line 65 is connected to a proximal portion of the first electric conducting portion 63A. One end of an electric signal line 66 is connected to a proximal portion of the second electric conducting portion 63B. One end of an electric signal line 67 is connected to a proximal portion of the third electric conducting portion 63C. The other ends of the electric signal lines 65 to 67 are connected to the controller 10 of the power supply unit 7 through the inside of the cable 6.

As described above, a first electric signal path is formed from the switch portion 58A to the controller 10 of the power supply unit 7 through the electric signal line 61A, the first electric connection portion 62A, the first electric conducting portion 63A, and the electric signal line 65. A second electric signal path is formed from the switch portion 58B to the controller 10 of the power supply unit 7 through the electric signal line 61B, the second electric connection portion 62B, the second electric conducting portion 63B, and the electric signal line 66. Moreover, a ground path is formed from the switch portion 58A and the switch portion 58B to the controller 10 through the electric signal line 61C, the third electric connection portion 62C, the third electric conducting portion 63C, and the electric signal line 67.

If the treatment mode input button 57A is pressed, the switch portion 58A is turned on (closed), and the first electric signal path is electrically connected to the ground path by the switch portion 58A. As a result, an electric signal is transmitted to the controller 10 of the power supply unit 7 from the switch portion 58A. An ultrasonic generating current is then output from the ultrasonic generating current supplier 8, and a high-frequency current is output from the high-frequency current supplier 9. That is, the first treatment mode is selected when the treatment mode input button 57A is pressed.

If the treatment mode input button 57B is pressed, the switch portion 58B is turned on (closed), and the second electric signal path is electrically connected to the ground path by the switch portion 58B. As a result, an electric signal is transmitted to the controller 10 of the power supply unit 7 from the switch portion 58B. A high-frequency current is then output from the high-frequency current supplier 9. In this case, no ultrasonic generating current is output from the ultrasonic generating current supplier 8. That is, the second treatment mode different from the first treatment mode is selected when the treatment mode input button 57B is pressed.

As shown in FIG. 6, the vibrator case 11 includes a fourth electric conducting portion 63D extending along the longitudinal axis C. All of the first electric conducting portion 63A, the second electric conducting portion 63B, and the third electric conducting portion 63C are electrically insulated from the fourth electric conducting portion 63D. An electric signal line 69 extending from the high-frequency current supplier 9 of the power supply unit 7 through the inside of the cable 6 is connected to a proximal portion of the fourth electric conducting portion 63D. When the vibrator case 11 is coupled to the movable cylindrical member 46 (the sheath body 41), a distal portion of the fourth electric conducting portion 63D alone is in electric contact with the movable cylindrical member 46. In this way, a high-frequency current is transmitted between the high-frequency current supplier 9 and the movable cylindrical member 46 of the sheath body 41 via the electric signal line 69 and the fourth electric conducting portion 63D.

As shown in FIG. 4, the sheath body 41 includes a fixed cylindrical member 71 located to the inner peripheral direction side of the rotational operation knob 37. The fixed cylindrical member 71 is fixed to the rotational operation knob 37, and is made of an insulating material such as a resin. A proximal portion of an outer tube 72 and a proximal portion of an outer pipe 73 are fixed to a distal portion of the fixed cylindrical member 71. The outer tube 72 is located to the outer peripheral direction side of the outer pipe 73, and forms an exterior of the sheath body 41 (the sheath unit 5). The outer tube 72 is made of an insulating material such as a resin. An inner tube 75 is provided to the inner peripheral direction side of the outer pipe 73. The inner tube 75 is made of an insulating material such as a resin, and is fixed to the outer pipe 73 via fixing pins 76A and 76B. The configuration described above allows the rotational operation knob 37 to be rotatable relative to the cylindrical case 31 together with the outer tube 72, the outer pipe 73, and the inner tube 75 in the directions around the longitudinal axis.

The sheath body 41 includes an inner pipe 77 provided between the outer pipe 73 and the inner tube 75 in diametrical directions. The inner pipe 77 is fixed to a distal portion of the movable cylindrical member 46 via a connection member 78 and a connection pin 79. The inner pipe 77 is movable relative to the outer tube 72, the outer pipe 73, and the inner tube 75 along the longitudinal axis C together with the movable cylindrical member 46. That is, the inner pipe 77 is movable relative to the handle unit 4 and the probe unit 3 along the longitudinal axis C together with the movable cylindrical member 46.

As the inner pipe 77 is fixed to the movable cylindrical member 46, a rotational operation in the rotational operation knob 37 is transmitted via the movable cylindrical member 46. Therefore, the inner pipe 77 is rotatable relative to the cylindrical case 31 in the directions around the longitudinal axis together with the rotational operation knob 37. As described above, the rotational operation knob 37 is rotatable relative to the cylindrical case 31 in the directions around the longitudinal axis together with the outer tube 72, the outer pipe 73, and the inner tube 75. Thus, the sheath body 41 is rotatable relative to the cylindrical case 31 in the directions around the longitudinal axis together with the rotational operation knob 37. The inner pipe 77 is made of an electrically conducting material such as a metal. A high-frequency current is transmitted between the movable cylindrical member 46 and the inner pipe 77 via the connection member 78 and the connection pin 79.

As shown in FIG. 4, the sheath unit 5 includes a movable plate 81 which is a movable portion provided to the inner peripheral direction side of the inner tube 75 along the longitudinal axis C. The movable plate 81 is inserted through the sheath body 41 (the inner tube 75), and is made of an electrically conducting material such as a metal. The movable plate 81 is movable relative to the probe body 21 (the probe unit 3) and the sheath body 41 along the longitudinal axis C. The movable plate 81 is fixed to a movement operation lever 83 which is a movement operation input portion via an intermediary portion 82 made of an electrically conducting material. The movement operation lever 83 is made of an insulating material. The movement operation lever 83 is coupled to the rotational operation knob 37 movably along the longitudinal axis C. If the movement operation lever 83 is moved relative to the rotational operation knob 37, the movable plate 81 moves relative to the probe body 21 and the sheath body 41 along the longitudinal axis C. That is, an operation to move the movable plate 81 which is the movable portion along the longitudinal axis C is input by the movement operation lever 83.

The movement operation lever 83 and the rotational operation knob 37 are coupled unrotatably relative to each other in the directions around the longitudinal axis. Thus, the movement operation lever 83 and the movable plate 81 are rotatable relative to the cylindrical case 31 in the directions around the longitudinal axis together with the rotational operation knob 37. As described above, the sheath body 41 is rotatable relative to the cylindrical case 31 in the directions around the longitudinal axis together with the rotational operation knob 37. Therefore, the sheath unit 5 (the sheath body 41 and the movable plate 81) are rotatable relative to the cylindrical case 31 in the directions around the longitudinal axis together with the rotational operation knob 37.

Figure 7:
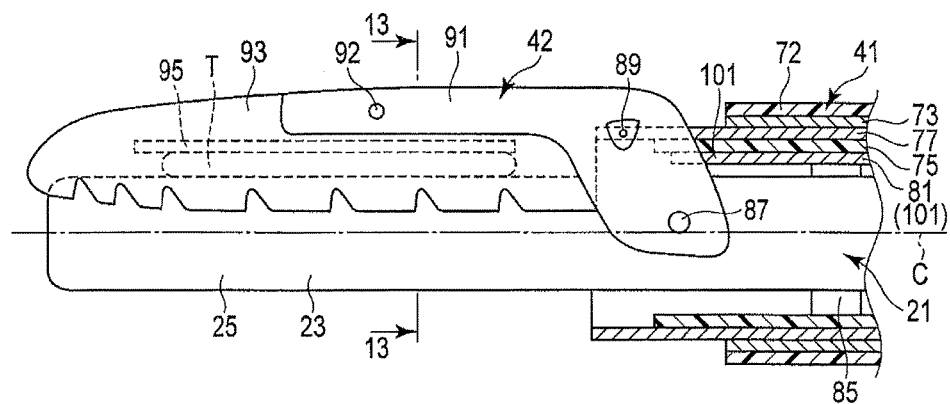
FIG. 7 is a partly sectional schematic view showing configurations of a distal portion of the probe unit, a distal portion of a sheath unit, and a jaw according to the first embodiment in a first treatment mode.
Figure 8:
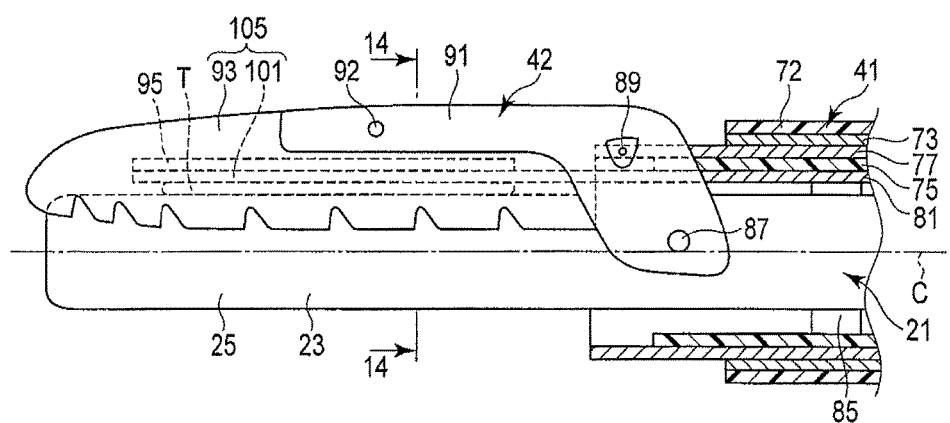
FIG. 8 is a partly sectional schematic view showing the configurations of the distal portion of the probe unit, the distal portion of the sheath unit, and the jaw according to the first embodiment in a second treatment mode.

FIG. 7 and FIG. 8 are diagrams showing the distal portion of the probe unit 3, the distal portion of the sheath unit 5, and the jaw 42. Here, FIG. 7 shows a state in which a living tissue T is grasped and treated in the first treatment mode, and FIG. 8 shows a state in which the living tissue T is grasped and treated in the second treatment mode. As shown in FIG. 7 and FIG. 8, the outer tube 72, the outer pipe 73, the inner tube 75, and the inner pipe 77 extend up to the distal portion of the sheath body 41 (the sheath unit 5) along the longitudinal axis C. As shown in FIG. 3, support members 85 made of an insulating material are formed on the outer peripheral portion of the probe body 21. The support members 85 are arranged apart from one another in directions parallel to the longitudinal axis C. When the probe body 21 is coupled to the horn 15, each of the support members 85 is located at the node position of the ultrasonic vibration.

The support members 85 prevent the contact between the movable plate 81 and the probe body 21 (the probe unit 3). The support members 85 also prevent the contact between the inner tube 75 (the sheath body 41) and the probe body 21 (the probe unit 3). As described above, the connection cylindrical member 45 and the elastic member 51 are made of an insulating material, so that the probe body 21 (the probe unit 3) is electrically insulated from the movable cylindrical member 46 (the sheath body 41). Therefore, the sheath unit 5 (the sheath body 41 and the movable plate 81) is electrically insulated from the probe unit 3 (the probe body 21) by the connection cylindrical member 45, the elastic member 51, and the support members 85.

As shown in FIG. 7 and FIG. 8, the jaw 42 is attached to the distal portion of the sheath body 41 (a distal portion of the outer tube 72 and a distal portion of the outer pipe 73) via a coupling pin 87. The jaw 42 is rotatable (pivotable) relative to the sheath body 41 around the coupling pin 87. A distal portion of the inner pipe 77 is coupled to the jaw 42 via a connection pin 89. A high-frequency current is transmitted between the inner pipe 77 and the jaw 42 via the connection pin 89. As described above, a high-frequency current can be transmitted to the jaw 42 from the high-frequency current supplier 9 through the electric signal line 69, the fourth electric conducting portion 63D, the movable cylindrical member 46, and the inner pipe 77.

FIG. 9 is a diagram showing the configuration of the jaw 42. FIG. 10 is a sectional view taken alone the line X-X in FIG. 9. In FIG. 10, the probe body 21 (the probe electric conducting portion 23) is also shown. As shown in FIG. 9 and FIG. 10, the jaw 42 includes a jaw body 91 attached to the sheath body 41. The jaw body 91 is made of an electrically conducting material. A jaw electric conducting portion 93 is coupled to the jaw body 91 via a connection pin 92. The high-frequency current transmitted to the jaw 42 from the inner pipe 77 of the sheath body 41 is transmitted to the jaw electric conducting portion 93 via the jaw body 91. When the high-frequency current is transmitted to the jaw electric conducting portion 93 through the sheath body 41 (the sheath unit 5), the jaw electric conducting portion 93 has a second electric potential E2 different in intensity from the first electric potential E1.

A pad member 95, which is an insulating abutting member, made of an insulating material is attached to the jaw electric conducting portion 93. The pad member 95 includes a jaw perpendicularly facing surface (abutting portion) 97 which is perpendicular to the opening-and-closing directions of the jaw 42. Jaw obliquely facing surfaces 98A and 98B are formed by the jaw electric conducting portion 93 on both sides of the jaw perpendicularly facing surface 97 in width directions which are directions perpendicular to the longitudinal axis C and perpendicular to the opening-and-closing directions of the jaw 42. In a section perpendicular to the longitudinal axis C, the jaw obliquely facing surfaces 98A and 98B are oblique to the jaw perpendicularly facing surface 97.

On the other hand, as shown in FIG. 10, the probe electric conducting portion 23 (the first electrode portion 25) includes a probe perpendicularly facing surface 102 which is perpendicular to the opening-and-closing directions of the jaw 42. The probe perpendicularly facing surface 102 is substantially parallel to the jaw perpendicularly facing surface 97, and faces the jaw perpendicularly facing surface 97. When the jaw 42 is closed relative to the probe electric conducting portion 23 while there is no grasping target such as a blood vessel (living tissue) between the probe electric conducting portion 23 (the first electrode portion 25) and the jaw 42 and while the movement operation lever 83 is located at a first operation position as described later, the jaw perpendicularly facing surface 97 abuts on the probe perpendicularly facing surface 102 of the probe electric conducting portion 23. That is, when the jaw 42 is closed relative to the probe electric conducting portion 23, the jaw perpendicularly facing surface (abutting portion) 97 can abut on the probe electric conducting portion 23.

Probe obliquely facing surfaces 103A and 103B are formed by the probe electric conducting portion 23 (the first electrode portion 25) on both sides of the probe perpendicularly facing surface 102 in the width directions which are the directions perpendicular to the longitudinal axis C and perpendicular to the opening-and-closing directions of the jaw 42. The probe obliquely facing surface 103A is substantially parallel to the jaw obliquely facing surface 98A, and the probe obliquely facing surface 103B is substantially parallel to the jaw obliquely facing surface 98B. A clearance is always formed between the probe obliquely facing surface 103A and the jaw obliquely facing surface 98A and between the probe obliquely facing surface 103B and the jaw obliquely facing surface 98B when the jaw 42 is closed relative to the probe electric conducting portion 23 while there is no grasping target such as a blood vessel (living tissue) between the probe electric conducting portion 23 (the first electrode portion 25) and the jaw 42 and while the movement operation lever 83 is located at the first operation position as described later. That is, there is a clearance between the jaw electric conducting portion 93 and the probe electric conducting portion 23 (the first electrode portion 25) when the jaw 42 is closed relative to the probe electric conducting portion 23 without any grasping target such as a blood vessel (living tissue) so that the jaw perpendicularly facing surface (abutting portion) 97 is brought in abutment with the probe electric conducting portion 23 (the probe perpendicularly facing surface 102).

Figure 11:
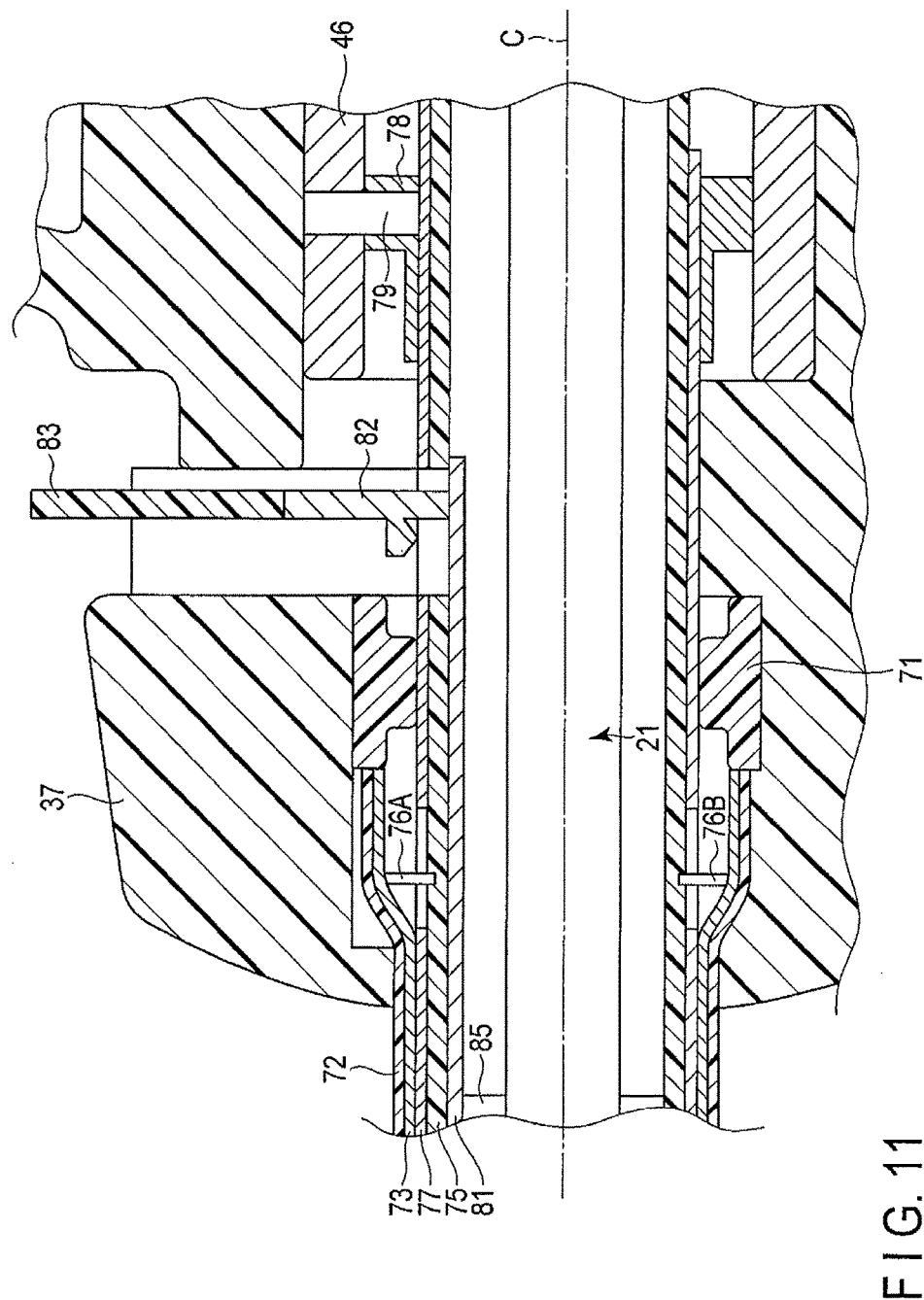
FIG. 11 is a schematic sectional view showing an internal configuration of a rotational operation knob in the first treatment mode.
Figure 12:
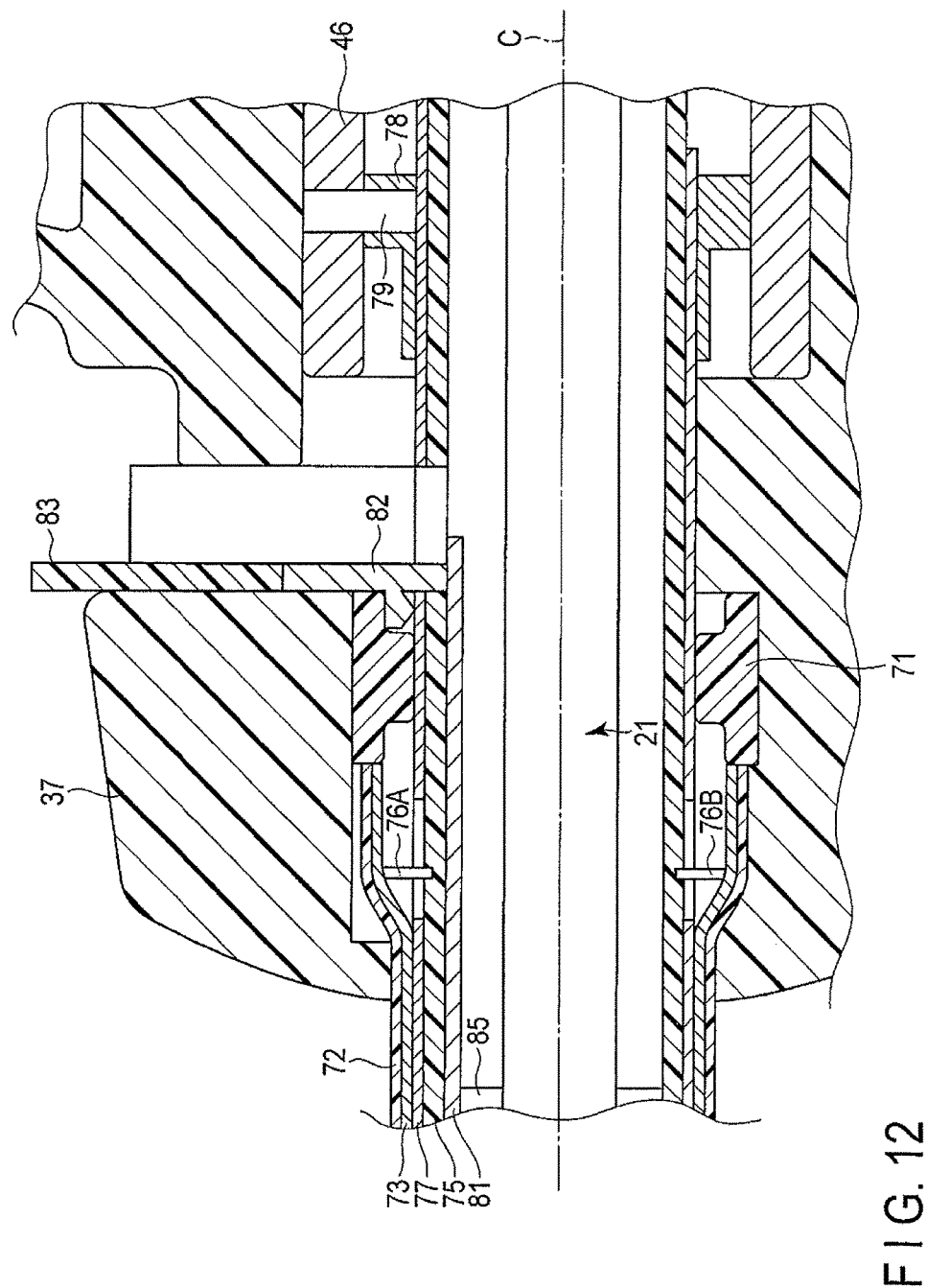
FIG. 12 is a schematic sectional view showing the internal configuration of the rotational operation knob in the second treatment mode.
Figure 13:
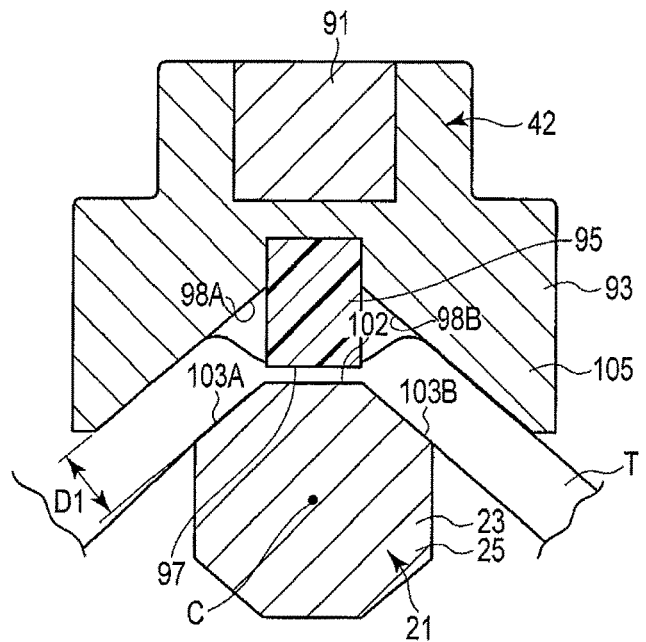
FIG. 13 is a sectional view taken along the line 13-13 in FIG. 7.
Figure 14:
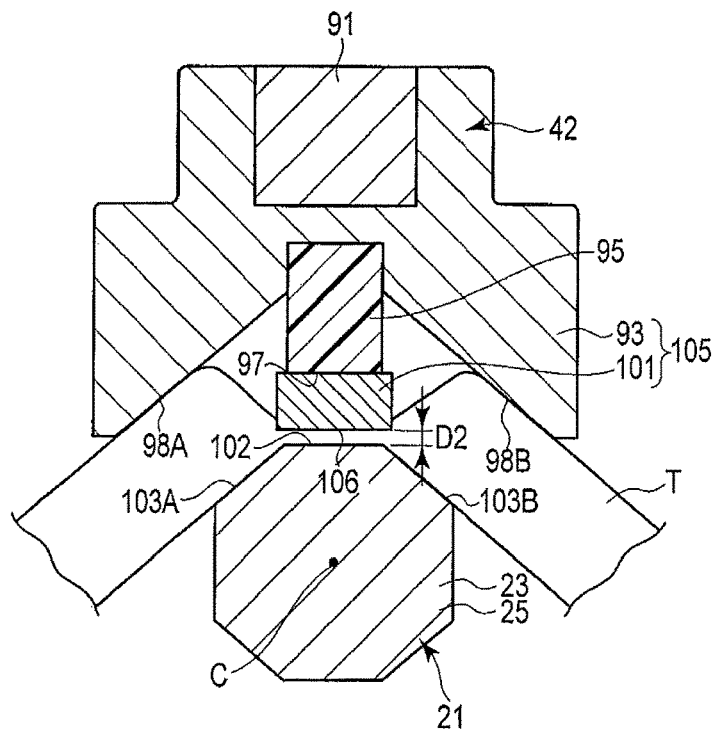
FIG. 14 is a sectional view taken along the line 14-14 in FIG. 8.

FIG. 11 and FIG. 12 are diagrams showing an internal configuration of the rotational operation knob 37. FIG. 11 shows the first treatment mode, and FIG. 12 shows the second treatment mode. FIG. 13 is a sectional view taken along the line 13-13 in FIG. 7. FIG. 14 is a sectional view taken along the line 14-14 in FIG. 8. As shown in FIG. 11, the movement operation lever 83 is located at the first operation position in the first treatment mode. In this case, the movable plate 81 and the intermediary portion 82 do not contact the inner pipe 77. Therefore, the movable plate 81 is electrically insulated from the inner pipe 77, and no high-frequency current is transmitted to the movable plate 81.

A movement electric conducting portion 101 is provided in a distal portion of the movable plate 81. In the first treatment mode, the movement electric conducting portion 101 is accommodated (housed) in the sheath body 41 as shown in FIG. 7 by an operation of moving the movement operation lever 83 to the first operation position. That is, the movement electric conducting portion 101 is located to the proximal direction side of the jaw 42.

In the first treatment mode, an ultrasonic generating current is then output from the ultrasonic generating current supplier 8. Thus, the ultrasonic vibration is generated in the ultrasonic vibrator 12, and transmitted to the probe electric conducting portion 23 (the distal portion of the probe unit 3). In the first treatment mode, a high-frequency current is output from the high-frequency current supplier 9. Thus, the high-frequency current is transmitted to the probe electric conducting portion 23, and the probe electric conducting portion 23 serves as the first electrode portion 25 having the first electric potential E1. The high-frequency current is also transmitted to the jaw electric conducting portion 93 of the jaw 42, and the jaw electric conducting portion 93 has the second electric potential E2. In this case, no high-frequency current is transmitted to the movable plate 81, and the movement electric conducting portion 101 therefore does not function as an electrode.

Consequently, in the first treatment mode, the jaw electric conducting portion 93 alone functions as a second electrode portion 105 having the second electric potential E2. In the first treatment mode, when the living tissue T is grasped, the distance between the first electrode portion 25 (the probe obliquely facing surfaces 103A and 103B) and the jaw electric conducting portion 93 (the jaw obliquely facing surfaces 98A and 98B) of the second electrode portion 105 is a first distance D1. That is, in the first treatment mode, the living tissue T is treated with high-frequency current at the first distance D1.

As shown in FIG. 12, in the second treatment mode, the movement operation lever 83 is moved from the first operation position toward the distal direction side, and is located at a second operation position. In this case, the intermediary portion 82 is in abutment with the inner pipe 77. Therefore, the movable plate 81 is electrically connected to the inner pipe 77, and a high-frequency current is transmitted to the movable plate 81. When the high-frequency current is transmitted to the movable plate 81, the movement electric conducting portion 101 has the second electric potential E2.

As shown in FIG. 8 and FIG. 14, in the second treatment mode, the movement electric conducting portion 101 is located between the jaw perpendicularly facing surface 97 (the jaw 42) and the probe perpendicularly facing surface 102 (the first electrode portion 25) in the opening-and-closing directions of the jaw 42 by an operation of moving the movement operation lever 83 to the second operation position. The movement electric conducting portion 101 includes a movable portion facing surface 106 perpendicular to the opening-and-closing directions of the jaw 42. In the second treatment mode in which the movement operation lever 83 is located at the second operation position, the movable portion facing surface 106 is substantially parallel to the probe perpendicularly facing surface 102, and faces the probe perpendicularly facing surface 102. Here, the distance between the movable portion facing surface 106 (the movement electric conducting portion 101) and the probe perpendicularly facing surface 102 (the first electrode portion 25) when the living tissue T is grasped is a second distance D2 smaller than the first distance D1.

In the second treatment mode, no ultrasonic generating current is output from the ultrasonic generating current supplier 8, and a high-frequency current is output from the high-frequency current supplier 9 alone. Thus, no ultrasonic vibration is generated in the ultrasonic vibrator 12. The high-frequency current is transmitted to the probe electric conducting portion 23, and the probe electric conducting portion 23 functions as the first electrode portion 25 having the first electric potential E1. The high-frequency current is also transmitted to the jaw electric conducting portion 93 of the jaw 42, and the jaw electric conducting portion 93 has the second electric potential E2. At the same time, the high-frequency current is transmitted to the movable plate (movable portion) 81, so that the movement electric conducting portion 101 also has the second electric potential E2.

Therefore, in the second treatment mode, the jaw electric conducting portion 93 and the movement electric conducting portion 101 function as the second electrode portion 105 having the second electric potential E2, and the movement electric conducting portion 101 serves as a part of the second electrode portion 105. Thus, in the second treatment mode, the distance between the first electrode portion 25 (the probe perpendicularly facing surface 102) and the movement electric conducting portion 101 (the movable portion facing surface 106) of the second electrode portion 105 when the living tissue T is grasped is the second distance D2 smaller than the first distance D1. That is, in the second treatment mode, the living tissue T can be treated with high-frequency current at the second distance D2 smaller than the first distance D1. In this way, the movement operation lever (movement operation input portion) 83 serves as an inter-electrode distance changing unit configured to change an inter-electrode distance so that the second distance D2 between the first electrode portion 25 and the second electrode portion 105 in the second treatment mode is smaller than the first distance D1 between the first electrode portion 25 and the second electrode portion 105 in the first treatment mode. That is, the distance between the two electrode portions (the first electrode portion 25 and the second electrode portion 105) is changed by the movement operation lever 83. In the second treatment mode, no ultrasonic vibration is transmitted to the probe electric conducting portion 23 (the distal portion of the probe unit 3), and a high-frequency current alone is transmitted to the first electrode portion 25 and the second electrode portion 105. In the second treatment mode, the distance between the first electrode portion 25 and the second electrode portion 105 is smaller, so that the living tissue T can be sufficiently treated (e.g., coagulated) with high-frequency current.

Figure 15:
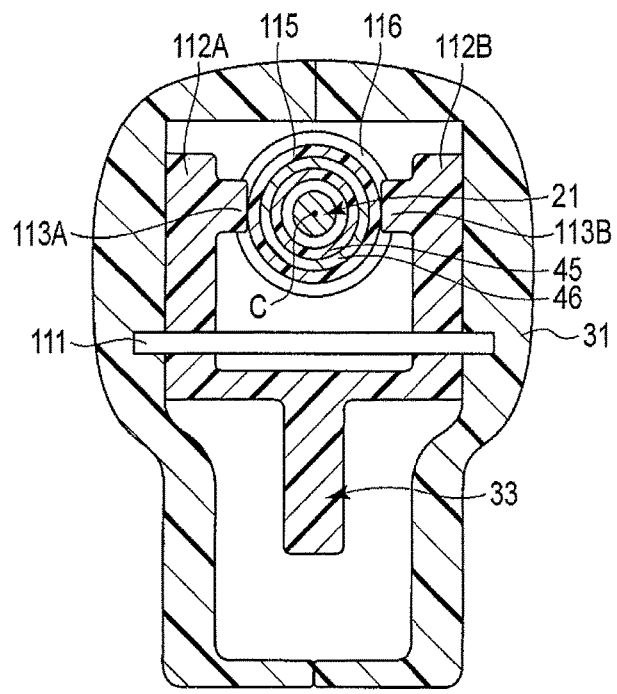
FIG. 15 is a sectional view taken along the line 15-15 in FIG. 4.

FIG. 15 is a sectional view taken along the line 15-15 in FIG. 4. As shown in FIG. 4 and FIG. 15, the movable handle 33 is attached to the cylindrical case 31 via a support pin 111. The movable handle 33 rotates relative to the cylindrical case 31 around the support pin 111. The movable handle 33 includes arms 112A and 112B. The arm 112A is provided with an engaging protrusion 113A protruding toward the inner peripheral direction, and the arm 112B is provided with an engaging protrusion 113B protruding toward the inner peripheral direction.

A slide member 115 is provided to the outer peripheral direction side of the movable cylindrical member 46. In the slide member 115, an engaging groove 116 which is depressed toward the inner peripheral direction is formed along the directions around the longitudinal axis. When the engaging protrusions 113A and 113B are engaged with the engaging groove 116, the movable handle 33 is attached to the slide member 115. The slide member 115 is rotatable relative to the movable handle 33 and the cylindrical case 31 in the directions around the longitudinal axis together with the movable cylindrical member 46 (the sheath body 41). The slide member 115 is made of an insulating material. Therefore, the movable cylindrical member 46 (the sheath body 41) is electrically insulated from the movable handle 33.

A coil spring 117 which is an elastic member and a stopper 118 are provided to the outer peripheral direction side of the movable cylindrical member 46. The coil spring 117 has one end connected to a distal end of the slide member 115, and the other end connected to the movable cylindrical member 46. The length of the coil spring 117 in a natural state is L0. When the jaw 42 is out of contact with the grasping target or the movement electric conducting portion 101, the coil spring 117 is attached between the movable cylindrical member 46 and the slide member 115 in a normal state in which the coil spring 117 has contracted from the natural state by a displacement amount x0. Thus, when the jaw 42 is out of contact with the grasping target or the movement electric conducting portion 101, elastic force k0x0 acts on the movable cylindrical member 46 from the coil spring 117 wherein the elastic coefficient of the coil spring 117 is k0. The movement of the slide member 115 toward the proximal direction is regulated by the stopper 118.

When the grasping target is grasped between the probe electric conducting portion 23 (the first electrode portion 25) and the jaw 42 in the first treatment mode or when the grasping target is grasped between the probe electric conducting portion 23 (the first electrode portion 25) and the movement electric conducting portion 101 in the second treatment mode, the movable handle 33 is closed relative to the fixed handle 32. As a result, the movable handle 33 rotates (pivots) around the support pin 111, and the slide member 115, the movable cylindrical member 46, and the inner pipe 77 move together toward the distal direction along the longitudinal axis C. In this case, the coil spring 117 does not contract from the normal state, and the elastic force acting on the movable cylindrical member 46 from the coil spring 117 does not change from k0x0. The jaw 42 is closed relative to the probe electric conducting portion 23 by the movement of the inner pipe 77 toward the distal direction.

When the jaw 42 has come into contact with a grasping target such as the living tissue T in the first treatment mode or when the jaw 42 has come into contact with the movement electric conducting portion 101 in the second treatment mode, the closing of the jaw 42 temporarily stops. Thus, the movement of the movable cylindrical member 46 and the inner pipe 77 toward the distal direction temporarily stops. When the movable handle 33 is further closed relative to the fixed handle 32 in this state, the slide member 115 moves relative to the movable cylindrical member 46 toward the distal direction.

The coil spring 117 further contracts from the normal state in response to the movement of the slide member 115 relative to the movable cylindrical member 46. The elastic force acting on the movable cylindrical member 46 from the coil spring 117 when the coil spring 117 has further contracted from the normal state is k0 (x0+x), wherein x is the displacement amount (contraction amount) of the coil spring 117 from the normal state. This elastic force is greater than the elastic force k0x0 in the normal state. As the elastic force k0 (x0+x) greater than the elastic force k0x0 in the normal state acts on the movable cylindrical member 46 from the coil spring 117, the movable cylindrical member 46 and the inner pipe 77 that have temporarily stopped further move toward the distal direction. As a result, the jaw 42 which has come into contact with the grasping target or the movement electric conducting portion 101 is further closed relative to the probe electric conducting portion 23. Therefore, a grasping force of grasping the grasping target between the jaw 42 and the probe electric conducting portion 23 (the first electrode portion 25) or between the movement electric conducting portion 101 and the probe electric conducting portion 23 (the first electrode portion 25) is greater than when the coil spring 117 is in the normal state.

When the movable handle 33 is opened relative to the fixed handle 32 from the state in which the grasping target is grasped between the jaw 42 and the probe electric conducting portion 23 or between the movement electric conducting portion 101 and the probe electric conducting portion 23, the slide member 115 moves relative to the movable cylindrical member 46 toward the proximal direction. Thus, the coil spring 117 spreads into the normal state. The slide member 115, the movable cylindrical member 46, and the inner pipe 77 then move together toward the proximal direction along the longitudinal axis C. The jaw 42 is opened relative to the probe electric conducting portion 23 by the movement of the inner pipe 77 toward the proximal direction.

Now, the functions of the grasping treatment device 1 according to the present embodiment are described. When the grasping treatment device 1 is used to conduct a treatment in the first treatment mode, the surgeon moves the movement operation lever 83 which is the movement operation input portion to the first operation position. As a result, the movement electric conducting portion 101 is accommodated (housed) in the sheath body 41, and located to the proximal direction side of the jaw 42. In this state, the movable handle 33 is closed relative to the fixed handle 32. Thus, the jaw 42 is closed relative to the probe electric conducting portion 23 of the probe body 21 (the probe unit 3) by the above-mentioned principle, and a grasping target such as a blood vessel is grasped between the jaw 42 and the probe electric conducting portion 23 (the first electrode portion 25).

The surgeon then presses the treatment mode input button 57A which is the treatment mode input portion, and the switch portion 58A is turned on (closed). As a result, the first electric signal path is electrically connected to the ground path by the switch portion 58A, and an electric signal is transmitted to the controller 10 of the power supply unit 7 from the switch portion 58A. An ultrasonic generating current is then output from the ultrasonic generating current supplier 8, and a high-frequency current is output from the high-frequency current supplier 9.

The ultrasonic vibration is generated in the ultrasonic vibrator 12 by the supply of a current to the ultrasonic vibrator 12 from the ultrasonic generating current supplier 8 via the electric signal lines 13A and 13B. The ultrasonic vibration is then transmitted to the probe electric conducting portion 23 (the distal portion of the probe unit 3). The grasping target grasped between the probe electric conducting portion 23 (the distal portion of the probe unit 3) and the jaw 42 is cut and coagulated by frictional heat generated by the ultrasonic vibration of the probe unit 3.

The high-frequency current output from the high-frequency current supplier 9 is transmitted to the probe electric conducting portion 23 through the electric signal line 17, the ultrasonic vibrator 12, the horn 15, and the probe body 21 (the probe unit 3). When the high-frequency current is transmitted to the probe electric conducting portion 23, the probe electric conducting portion 23 functions as the first electrode portion 25 having the first electric potential E1.

A high-frequency current is also transmitted to the jaw electric conducting portion 93 from the high-frequency current supplier 9 through the electric signal line 69, the fourth electric conducting portion 63D, the movable cylindrical member 46, the inner pipe 77, and the jaw 42. When the high-frequency current is transmitted to the jaw electric conducting portion 93, the jaw electric conducting portion 93 has the second electric potential E2 different in intensity from the first electric potential E1. When the movement operation lever 83 is located at the first operation position, the movable plate 81 is electrically insulated from the movable cylindrical member 46. Thus, no high-frequency current is transmitted to the movable plate 81, and the movement electric conducting portion 101 does not function as an electrode. Therefore, in the first treatment mode, the jaw electric conducting portion 93 alone functions as the second electrode portion 105 having the second electric potential E2.

The probe electric conducting portion 23 (the first electrode portion 25) has the first electric potential E1, and the jaw electric conducting portion 93 (the second electrode portion 105) has the second electric potential E2, so that a high-frequency current runs through the grasping target grasped between the probe electric conducting portion 23 and the jaw 42. Consequently, a grasping target such as the living tissue T is reformed, and the coagulation is accelerated.

In the first treatment mode, the movement electric conducting portion 101 is located to the proximal direction side of the jaw 42, so that the probe electric conducting portion 23 (the probe obliquely facing surfaces 103A and 103B) of the first electrode portion 25 and the jaw electric conducting portion 93 (the jaw obliquely facing surfaces 98A and 98B) of the second electrode portion 105 is the first distance D1. Even when the probe body 21 (the probe unit 3) is being ultrasonically vibrated, the first electrode portion 25 and the second electrode portion 105 (the jaw electric conducting portion 93) do not contact with being spaced by the first distance D1. This effectively prevents the breakdown of the grasping treatment device 1 caused by a short circuit. Moreover, the probe body 21 is ultrasonically vibrated in the first treatment mode. Thus, the pad member 95 which can abut on the probe electric conducting portion 23 when the jaw 42 is closed relative to the probe electric conducting portion 23 is worn by the treatment in the first treatment mode. Thus, the first distance D1 prevents the contact between the probe electric conducting portion 23 (the first electrode portion 25) and the jaw electric conducting portion 93 (the second electrode portion 105) from the start of the use of the grasping treatment device 1 even if the pad member 95 is slightly worn by the treatment in the first treatment mode.

When the grasping treatment device 1 is used to conduct a treatment in the second treatment mode, the surgeon moves the movement operation lever 83 which is the movement operation input portion to the second operation position. As a result, the movement electric conducting portion 101 is located between the jaw perpendicularly facing surface 97 (the jaw 42) and the probe perpendicularly facing surface 102 (the first electrode portion 25) in the opening-and-closing directions of the jaw 42.

In this state, the movable handle 33 is closed relative to the fixed handle 32. Thus, the jaw 42 is closed relative to the probe electric conducting portion 23 of the probe body 21 (the probe unit 3) by the above-mentioned principle, and a grasping target such as a blood vessel is grasped between the movement electric conducting portion 101 and the probe electric conducting portion 23 (the first electrode portion 25). At this time, the jaw 42 contacts the movement electric conducting portion 101, and the movement electric conducting portion 101 is thereby pressed by the jaw 42 toward the closing direction of the jaw 42. As a result, the grasping target is held between the probe electric conducting portion 23 (the first electrode portion 25) and the movement electric conducting portion 101, and the grasping target is grasped.

The surgeon then presses the treatment mode input button 57B which is the second treatment mode input portion, and the switch portion 58B is turned on (closed). As a result, the second electric signal path is electrically connected to the ground path by the switch portion 58B, and an electric signal is transmitted to the controller 10 of the power supply unit 7 from the switch portion 58B. A high-frequency current is then output from the high-frequency current supplier 9. In this case, no current is output from the ultrasonic generating current supplier 8.

The high-frequency current output from the high-frequency current supplier 9 is transmitted to the probe electric conducting portion 23 through the electric signal line 17, the ultrasonic vibrator 12, the horn 15, and the probe body 21 (the probe unit 3). When the high-frequency current is transmitted to the probe electric conducting portion 23, the probe electric conducting portion 23 functions as the first electrode portion 25 having the first electric potential E1.

A high-frequency current is also transmitted to the jaw electric conducting portion 93 from the high-frequency current supplier 9 through the electric signal line 69, the fourth electric conducting portion 63D, the movable cylindrical member 46, the inner pipe 77, and the jaw 42. When the high-frequency current is transmitted to the jaw electric conducting portion 93, the jaw electric conducting portion 93 has the second electric potential E2 different in intensity from the first electric potential E1.

When the movement operation lever 83 is located at the second operation position, the movable plate 81 is electrically connected to the inner pipe 77 (the movable cylindrical member 46). Thus, a high-frequency current is transmitted to the movable plate 81, and the movement electric conducting portion 101 functions as the second electrode portion 105 having the second electric potential E2. Therefore, in the second treatment mode, the jaw electric conducting portion 93 and the movement electric conducting portion 101 function as the second electrode portion 105 having the second electric potential E2, and the movement electric conducting portion 101 serves as a part of the second electrode portion 105. Moreover, in the second treatment mode, no ultrasonic vibration is transmitted to the probe electric conducting portion 23 (the distal portion of the probe unit 3), and a high-frequency current alone is transmitted to the first electrode portion 25 and the second electrode portion 105.

The first electrode portion 25 (the probe electric conducting portion 23) has the first electric potential E1, and the second electrode portion 105 (the jaw electric conducting portion 93 and the mobile electric conducting portion 101) has the second electric potential E2, so that a high-frequency current also runs through the grasping target grasped between the probe electric conducting portion 23 and the movement electric conducting portion 101. Consequently, a grasping target such as the living tissue T is reformed and coagulated.

In the second treatment mode, the movement electric conducting portion 101 (the jaw 42) is located between the jaw 42 and the first electrode portion 25 in the opening-and-closing directions of the jaw 42. Therefore, the distance between the probe electric conducting portion 23 (the probe perpendicularly facing surface 102) of the first electrode portion 25 and the movement electric conducting portion 101 (the movable portion facing surface 106) of the second electrode portion 105 is the second distance D2. The second distance D2 is smaller than the first distance D1. That is, the distance between the first electrode portion 25 and the second electrode portion 105 is smaller in the second treatment mode than in the first treatment mode. Since the distance between the first electrode portion 25 and the second electrode portion 105 is smaller, the reformation of the living tissue T (grasping target) with the high-frequency current is more accelerated in the second treatment mode than in the first treatment mode. Therefore, the performance of the coagulation of the grasping target with the high-frequency current is improved, so that the deterioration in the performance of the coagulation of the grasping target is prevented in the second treatment mode, which does not use the ultrasonic vibration. Consequently, the grasping target (living tissue) is stably sealed in the second treatment mode, which does not use the ultrasonic vibration.

In the second treatment mode, the movement electric conducting portion 101 is located between the jaw perpendicularly facing surface (abutting portion) 97 and the probe perpendicularly facing surface 102 in the opening-and-closing directions of the jaw 42. The grasping target is grasped between the movement electric conducting portion 101 and the probe electric conducting portion 23 (the first electrode portion 25). The probe perpendicularly facing surface 102 of the probe electric conducting portion 23 is perpendicular to the opening-and-closing directions of the jaw 42. The movable portion facing surface 106 of the movement electric conducting portion 101 is substantially parallel to the probe perpendicularly facing surface 102, and faces the probe perpendicularly facing surface 102. Since the probe perpendicularly facing surface 102 and the movable portion facing surface 106 are perpendicular to the opening-and-closing directions of the jaw 42, the grasping force to grasp the grasping target between the movement electric conducting portion 101 and the probe electric conducting portion 23 (the first electrode portion 25) is greater. The greater grasping force further improves the performance of the coagulation of the grasping target with the high-frequency current. Consequently, the grasping target (living tissue) is more stably sealed.

Accordingly, the grasping treatment device 1 having the configuration described above has the following advantageous effects. In the grasping treatment device 1, in the second treatment mode, the movement electric conducting portion 101 is located between the jaw 42 and the probe electric conducting portion 23 (the first electrode portion 25) in the opening-and-closing directions of the jaw 42. Thus, the distance between the probe electric conducting portion 23 (the probe perpendicularly facing surface 102) of the first electrode portion 25 and the movement electric conducting portion 101 (the movable portion facing surface 106) of the second electrode portion 105 is the second distance D2. The second distance D2 is smaller than the first distance D1. That is, the distance between the first electrode portion 25 and the second electrode portion 105 is smaller in the second treatment mode than in the first treatment mode. Since the distance between the first electrode portion 25 and the second electrode portion 105 is smaller, the reformation of the living tissue T (grasping target) with the high-frequency current is more accelerated in the second treatment mode than in the first treatment mode. Therefore, the performance of the coagulation of the grasping target with the high-frequency current is improved so that the deterioration in the performance of the coagulation of the grasping target is prevented in the second treatment mode, which does not use the ultrasonic vibration. Consequently, the grasping target (living tissue) is stably sealed in the second treatment mode, which does not use the ultrasonic vibration.

(Modification of First Embodiment)

Figure 16:
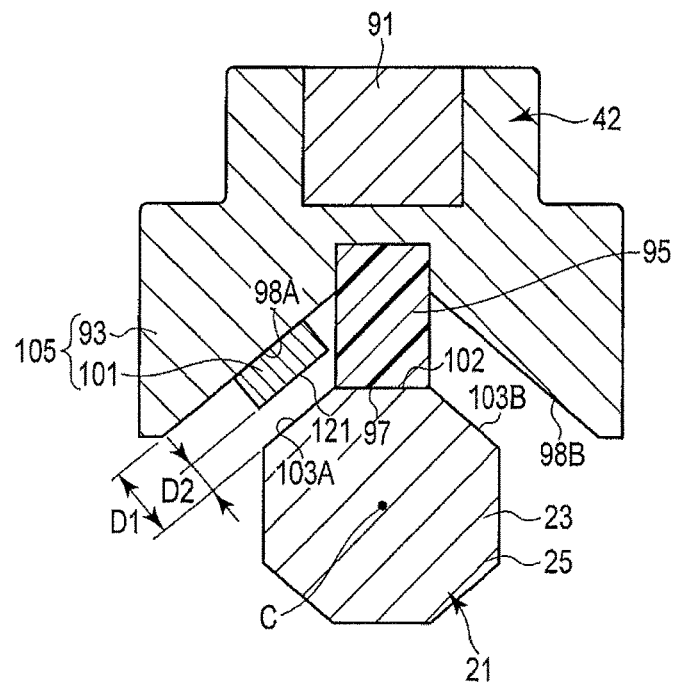
FIG. 16 is a schematic sectional view showing configurations of a distal portion of a probe unit, a distal portion of a sheath unit, and a jaw according to a first modification of the first embodiment in the second treatment mode.

According to the first embodiment, in the second treatment mode, the movement electric conducting portion 101 is located between the jaw perpendicularly facing surface (abutting portion) 97 and the probe perpendicularly facing surface 102 in the opening-and-closing directions of the jaw 42, and the movable portion facing surface 106 of the movement electric conducting portion 101 is perpendicular to the opening-and-closing directions of the jaw 42. However, the present invention is not limited to this. For example, as in a first modification shown in FIG. 16, in the second treatment mode, the movement electric conducting portion 101 may be located between the jaw obliquely facing surface 98A and the probe obliquely facing surface 103A in the opening-and-closing directions of the jaw 42. In FIG. 16, the grasping target T grasped between the jaw 42 and the probe body 21 (the probe electric conducting portion 23) is not shown.

In the present modification, the movement electric conducting portion 101 includes a movable portion facing surface 121 substantially parallel to the jaw obliquely facing surface 98A and the probe obliquely facing surface 103A. The movable portion facing surface 121 is not perpendicular to the opening-and-closing directions of the jaw 42, and faces the probe obliquely facing surface 103A in the second treatment mode.

In the present modification as well, the movement electric conducting portion 101 is located to the proximal direction side of the jaw 42 in the first treatment mode. Thus, the distance between the probe obliquely facing surface 103A and the jaw obliquely facing surface 98A (the distance between the probe obliquely facing surface 103B and the jaw obliquely facing surface 98B) is the first distance D1 between the first electrode portion 25 (the probe electric conducting portion 23) and the second electrode portion 105 (the jaw electric conducting portion 93) in the first treatment mode. In the second treatment mode, the movement electric conducting portion 101 is located between the jaw obliquely facing surface 98A and the probe obliquely facing surface 103A in the opening-and-closing directions of the jaw 42. Thus, the distance between the movable portion facing surface 121 and the probe obliquely facing surface 103A is the second distance D2 between the first electrode portion 25

(the probe electric conducting portion 23) and the second electrode portion 105 (the movement electric conducting portion 101) in the second treatment mode.

As described above, in the present modification as well, the distance between the first electrode portion 25 and the second electrode portion 105 is smaller in the second treatment mode than in the first treatment mode. Since the distance between the first electrode portion 25 and the second electrode portion 105 is smaller, the reformation of the living tissue T (grasping target) with the high-frequency current is more accelerated in the second treatment mode than in the first treatment mode.

Although the movable plate 81 is moved by the operation to move the movement operation lever 83 between the first operation position and the second operation position along the longitudinal axis C in the first embodiment, the present invention is not limited to this. For example, as in a second modification shown in FIG. 17 and FIG. 18, a movement operation button 122 may be provided as the movement operation input portion. The movement operation button 122 is made of an insulating material, and is attached to the rotational operation knob 37 so that the rotation relative to the rotational operation knob 37 in the directions around the longitudinal axis is regulated. An intermediary portion 123 made of an electrically conducting material is provided to the inner peripheral direction side of the movement operation button 122 integrally with the movement operation button 122.

The movable plate (movable portion) 81 is provided between the inner tube 75 and the probe body 21 (the probe unit 3). The movable plate 81 is provided movably relative to the probe body 21 and the sheath body 41 along the longitudinal axis C. The movable plate 81 is electrically insulated from the probe body 21 by the support members 85. A button-side inclined surface 125A is provided in the intermediary portion 123. A plate-side inclined surface 125B parallel to the button-side inclined surface 125A is provided in a proximal portion of the movable plate 81.

A protrusion 127 which is made of an insulating material and which protrudes toward the inner peripheral direction is provided on the inner peripheral portion of the rotational operation knob 37. The protrusion 127 is located to the proximal direction side of a proximal end of the movable plate 81. A spring member 128 which is an urging member is provided between the protrusion 127 and the movable plate 81. The spring member 128 has one end connected to the proximal end of the movable plate 81, and the other end connected to the protrusion 127. The movable plate 81 is urged toward the proximal direction by the spring member 128.

Figure 17:
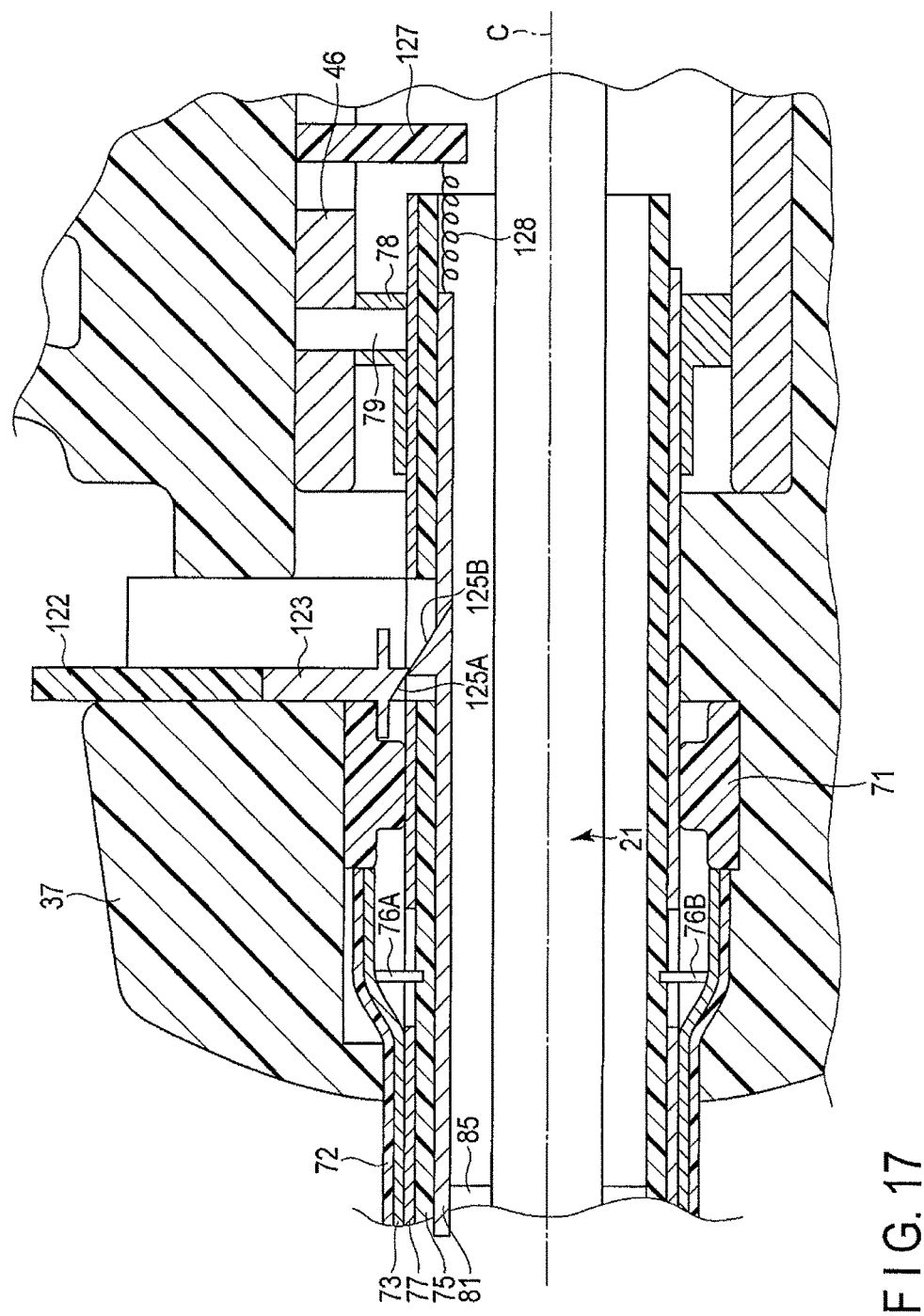
FIG. 17 is a schematic sectional view showing an internal configuration of a rotational operation knob according to a second modification of the first embodiment in the first treatment mode.

As shown in FIG. 17, in the first treatment mode, the movement operation button 122 is not pressed by the surgeon, and the movement operation button 122 is located at the first operation position. In this case, the button-side inclined surface 125A of the intermediary portion 123 and the plate-side inclined surface 125B of the movable plate 81 are not in abutment or are partly in contact. Thus, the movable plate 81 is not pressed by the intermediary portion 123. The movable plate 81 is urged toward the proximal direction by the spring member 128. Therefore, the movement electric conducting portion 101 provided in the distal portion of the movable plate 81 is accommodated (housed) in the sheath body 41, and located to the proximal direction side of the jaw 42.

Figure 18:
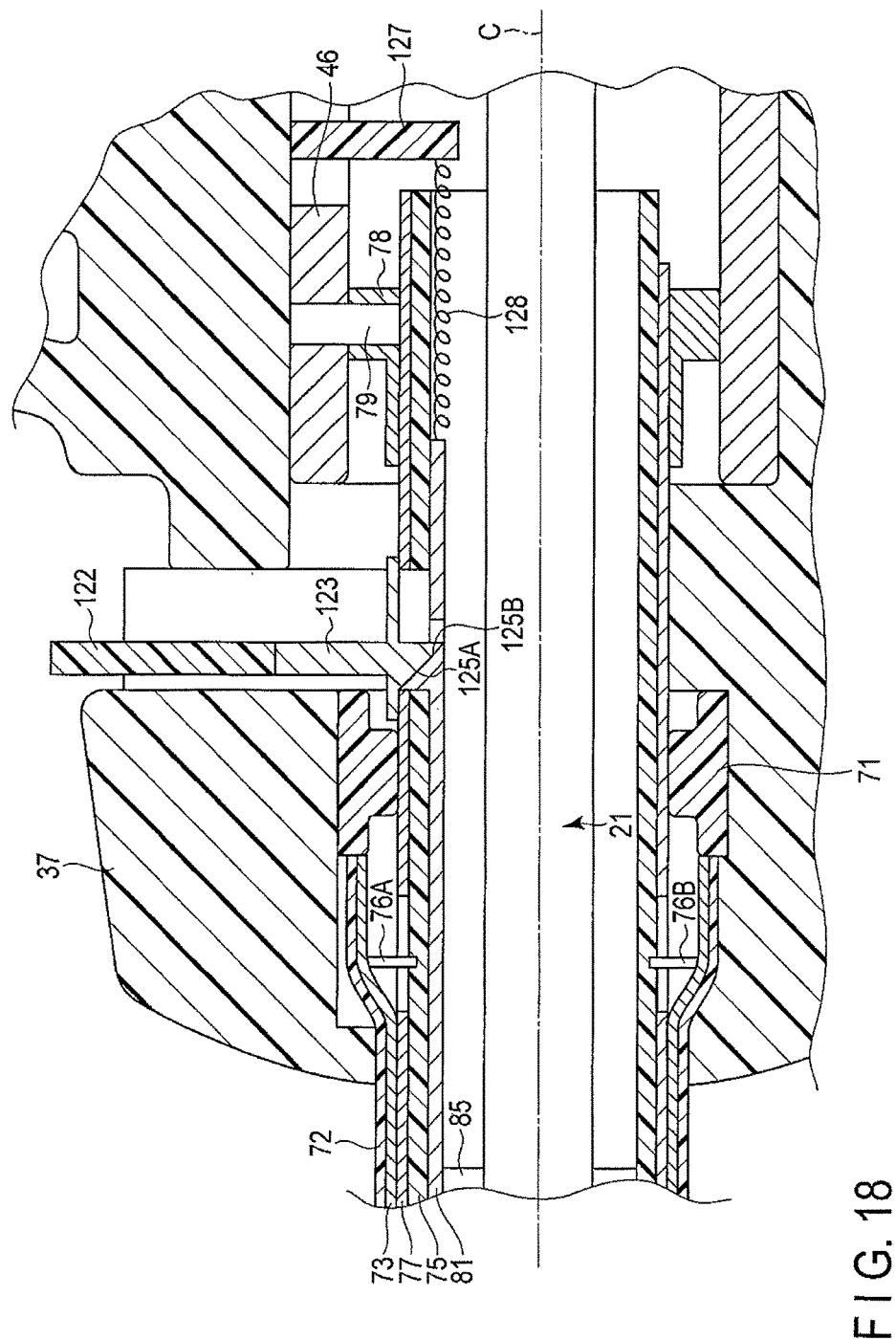
FIG. 18 is a schematic sectional view showing the internal configuration of the rotational operation knob according the second modification of the first embodiment in the second treatment mode.

As shown in FIG. 18, in the second treatment mode, the surgeon presses the movement operation button 122 toward the inner peripheral direction, and the movement operation button 122 is thereby moved to the second operation position from the first operation position. As a result, a button-side inclined surface 127A of the intermediary portion 123 abuts on the plate-side inclined surface 127B of the movable plate 81. In this case, the movable plate 81 is pressed toward the distal direction. Thus, the movable plate 81 moves toward the distal direction against the urging from the spring member 128. Therefore, the movement electric conducting portion 101 provided in the distal portion of the movable plate 81 is located between the jaw 42 and the probe electric conducting portion 23 (the first electrode portion 25) in the opening-and-closing directions of the jaw 42.

As described above, according to the first modification and the second modification, the configuration which allows the distance between the first electrode portion 25 and the second electrode portion 105 to be smaller in the second treatment mode than in the first treatment mode is not limited to the first embodiment. That is, the movable portion (the movable plate 81) has only to be provided to be inserted in the sheath body 41, and the movable portion (the movable plate 81) has only to be movable relative to the probe body 21 and the sheath body 41 along the longitudinal axis C. The movement electric conducting portion 101 has only to be provided in the distal portion of the movable portion (the movable plate 81), and the movement operation input portion (the movement operation lever 83 or the movement operation button 122) to which an operation of moving the movable portion is input has only to be provided. In this case, in the first treatment mode, the movement electric conducting portion 101 is located to the proximal direction side of the jaw 42 by the operation in the movement operation input portion. In the second treatment mode, the movement electric conducting portion 101 is located between the jaw 42 and the first electrode portion 25 in the opening-and-closing directions of the jaw 42 by the operation in the movement operation input portion. Moreover, in the second treatment mode, the high-frequency current is transmitted through the movable portion (the movable plate 81), and the movement electric conducting portion 101 functions as at least a part of the second electrode portion 105.

(Second Embodiment)

Now, a second embodiment of the present invention is described with reference to FIG. 19 to FIG. 22. In the second embodiment, the configuration according to the first embodiment is modified as below. The same parts as those in the first embodiment are provided with the same reference signs, and are not described.

FIG. 19 and FIG. 20 are diagrams showing the configurations of the distal portion of a probe unit 3 and a jaw 42. FIG. 19 shows a state in which a living tissue T is grasped and treated in a first treatment mode. FIG. 20 shows a state in which the living tissue T is grasped and treated in a second treatment mode. As shown in FIG. 19 and FIG. 20, a probe electric conducting portion 23 is provided in the distal portion of a probe body 21 of the probe unit 3, as in the first embodiment.

Figure 21:
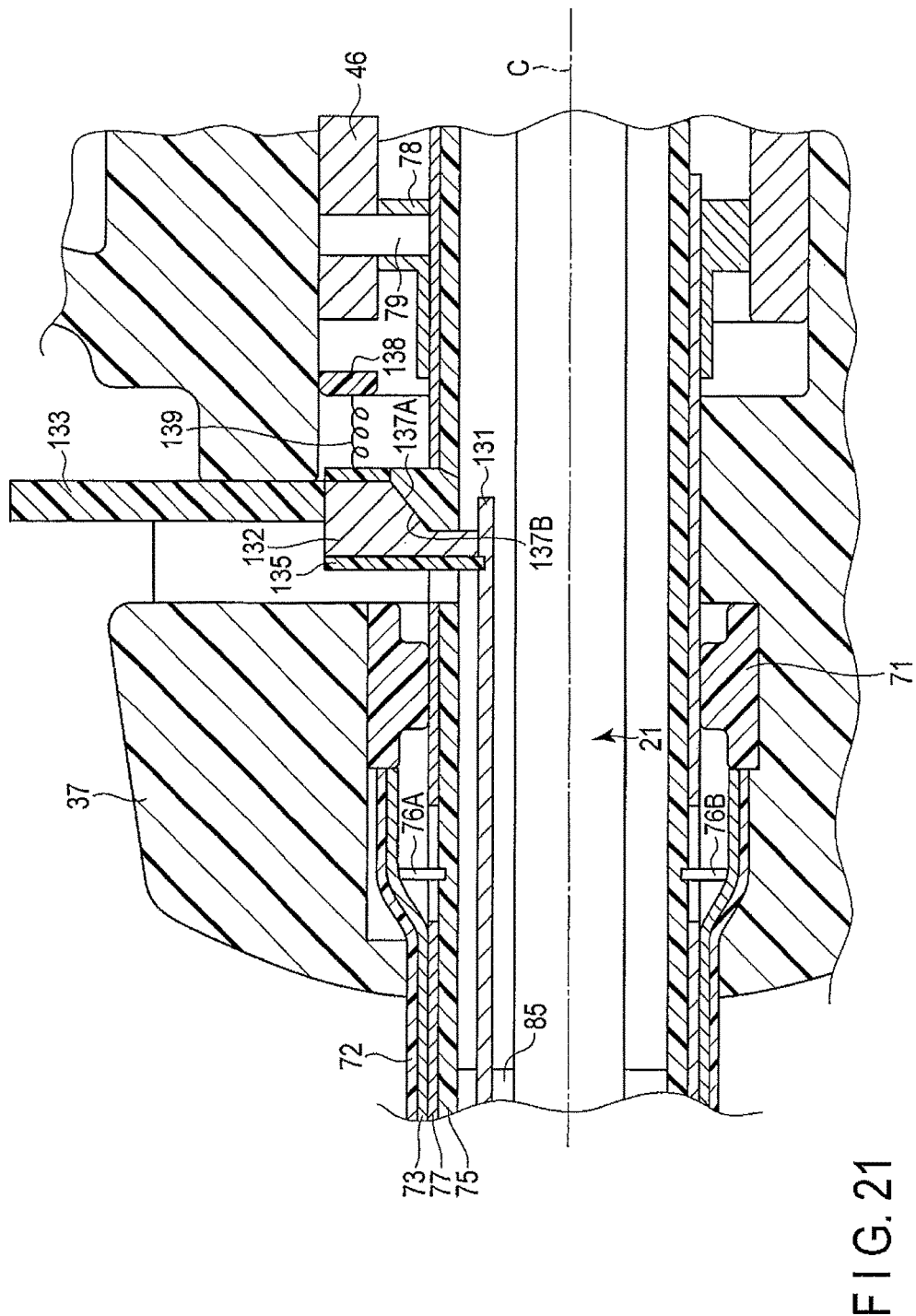
FIG. 21 is a schematic sectional view showing an internal configuration of a rotational operation knob according the second embodiment in the first treatment mode.
Figure 22:
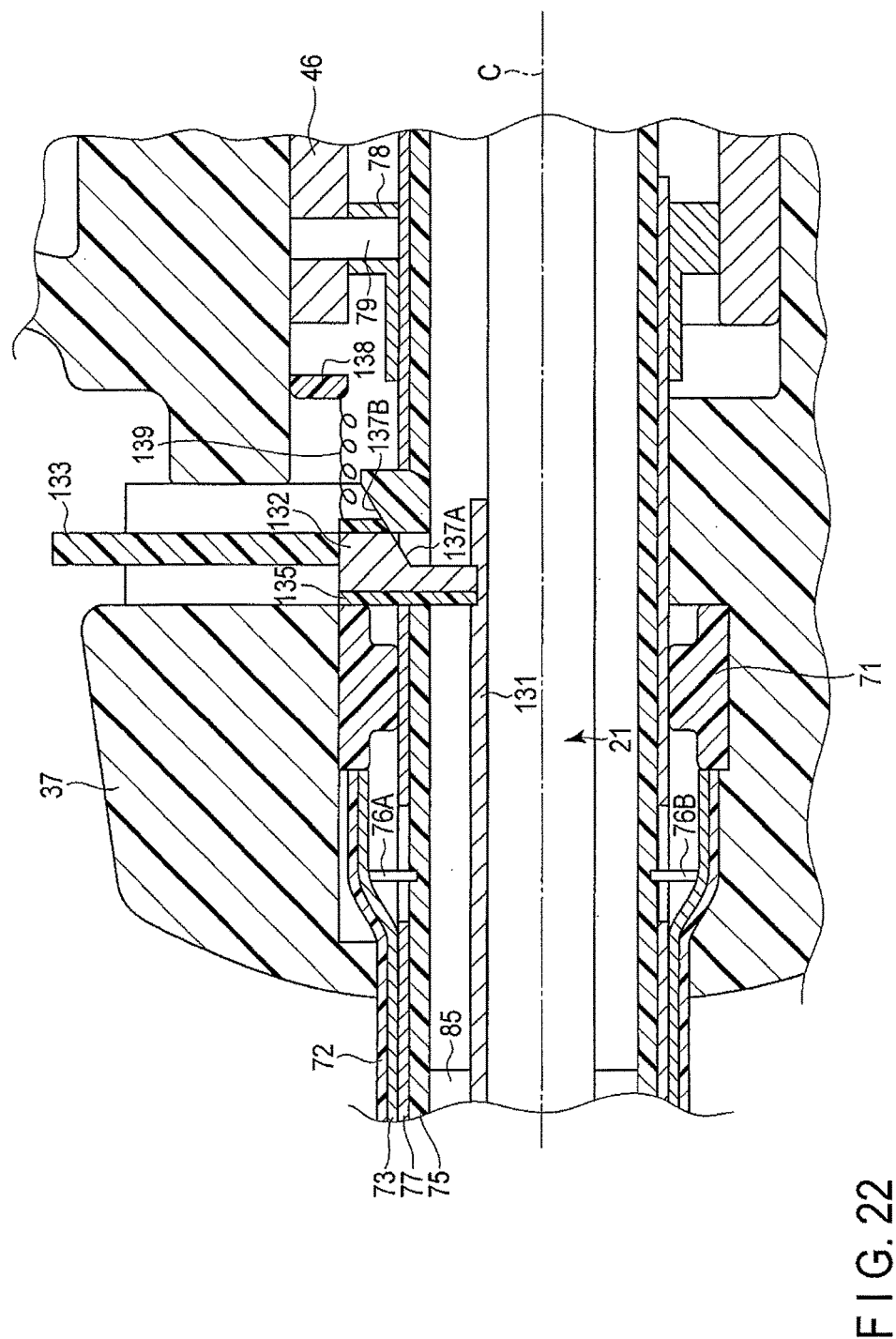
FIG. 22 is a schematic sectional view showing the internal configuration of the rotational operation knob according the second embodiment in the second treatment mode.

FIG. 21 and FIG. 22 are diagrams showing an internal configuration of a rotational operation knob 37. FIG. 21 shows the first treatment mode, and FIG. 22 shows the second treatment mode. As shown in FIG. 21 and FIG. 22, the probe unit 3 inserted through a sheath body 41 includes a movable plate 131 which is a movable portion provided to the inner peripheral direction side of an inner tube 75 along the longitudinal axis C. The movable plate 131 is made of an electrically conducting material such as a metal. The movable plate 131 is movable relative to the probe body 21 and the sheath body 41 (a sheath unit 5) along the longitudinal axis C. The movable plate 131 is electrically insulated from the sheath body 41 (an inner pipe 77) by the inner tube 75. The probe body 21 is electrically insulated from the sheath body 41 by support members 85 and the inner tube 75. Therefore, the probe unit 3 is electrically insulated from the sheath unit 5.

The movable plate 131 is fixed to a movement operation button 133 which is the movement operation input portion via an intermediary portion 132 made of an electrically conducting material. The movement operation button 133 is made of an insulating material. The movement operation button 133 is coupled to the rotational operation knob 37 so that the rotation relative to the rotational operation knob 37 in the directions around the longitudinal axis is regulated. A surface of the intermediary portion 132 is partly coated for insulation, and an insulating layer 135 is formed thereon. The contact between the inner pipe 77 and the intermediary portion 132 is always prevented by the provision of the insulating layer 135. Thus, the movable plate 131 is always insulated from the inner pipe 77 (the sheath unit 5). A plate-side inclined surface 137A is provided in the intermediary portion 132. A sheath-side inclined surface 137B parallel to the plate-side inclined surface 137A is provided in a proximal portion of the inner tube 75 of the sheath body 41.

A protrusion 138 which is made of an insulating material and which protrudes toward the inner peripheral direction is provided on the inner peripheral portion of the rotational operation knob 37. The protrusion 138 is located to the proximal direction side of a proximal end of the intermediary portion 132. A spring member 139 which is an urging member is provided between the protrusion 138 and the intermediary portion 132. The spring member 139 has one end connected to the insulating layer 135, and the other end connected to the protrusion 138. The intermediary portion 132 and the movable plate 131 are urged toward the proximal direction by the spring member 139.

The movable plate 131 moves relative to the probe body 21 and the sheath body 41 along the longitudinal axis C by the operation in the movement operation button 133. That is, an operation of moving the movable plate 131 which is the movable portion along the longitudinal axis C is input by the movement operation button 133.

As shown in FIG. 21, in the first treatment mode, the movement operation button 133 is not pressed by the surgeon, and the movement operation button 133 is located at the first operation position. In this case, the plate-side inclined surface 137A of the intermediary portion 132 and the sheath-side inclined surface 137B of the inner tube 75 are in abutment. The movable plate 131 is urged toward the proximal direction by a spring member 129. A movement electric conducting portion 141 is provided in the distal portion of the movable plate 131. In the first treatment mode in which the movement operation button 133 is located at the first operation position, the movable plate 131 is urged toward the proximal direction, so that the movement electric conducting portion 141 is accommodated in the sheath body 41. That is, the movement electric conducting portion 141 is located to the proximal direction side of the jaw 42 (see FIG. 19).

When the movement operation button 133 is located at the first operation position, the movable plate 131 and the intermediary portion 132 do not contact the probe body 21. Therefore, the movable plate 131 is electrically insulated from the probe body 21, and no high-frequency current is transmitted to the movable plate 131 from the probe body 21.

As shown in FIG. 19, the probe electric conducting portion 23 includes a probe perpendicularly facing surface 102, and probe obliquely facing surfaces 103A and 103B, as in the first embodiment. As in the first embodiment, when the high-frequency current is transmitted to the probe electric conducting portion 23, the probe electric conducting portion 23 functions as a first electrode portion 25 having a first electric potential E1.

A jaw perpendicularly facing surface 142 parallel to the probe perpendicularly facing surface 102 is formed in the jaw 42 by a jaw electric conducting portion 93. The probe perpendicularly facing surface 102 faces the jaw perpendicularly facing surface 142 in the first treatment mode. A first jaw obliquely facing surface 143A is formed by the pad member 95 on one side of the jaw perpendicularly facing surface 142 in width directions which are directions perpendicular to the longitudinal axis C and perpendicular to the opening-and-closing directions of the jaw 42. A second jaw obliquely facing surface 143B is formed by the jaw electric conducting portion 93 on the other side of the jaw perpendicularly facing surface 142 in the width directions. The first jaw obliquely facing surface 143A is substantially parallel to a probe obliquely facing surface 103A, and faces the probe obliquely facing surface 103A. The second jaw obliquely facing surface 143B is substantially parallel to a probe obliquely facing surface 103B, and faces the probe obliquely facing surface 103B.

When the jaw 42 is closed relative to the probe electric conducting portion 23 while there is no grasping target such as a blood vessel (living tissue) between the probe electric conducting portion 23 (the first electrode portion 25) and the jaw 42 and while the movement operation button 133 is located at the first operation position, the first jaw obliquely facing surface 143A abuts on the probe obliquely facing surface 103A of the probe electric conducting portion 23. That is, when the jaw 42 is closed relative to the probe electric conducting portion 23, the first jaw obliquely facing surface (abutting portion) 143A can abut on the probe electric conducting portion 23. A clearance is always formed between the probe obliquely facing surface 103B and the second jaw obliquely facing surface 143B and between the probe perpendicularly facing surface 102 and the jaw perpendicularly facing surface 142 when the jaw 42 is closed relative to the probe electric conducting portion 23. That is, there is a clearance between the jaw electric conducting portion 93 (the jaw perpendicularly facing surface 142 and the second jaw obliquely facing surface 143B) and the probe electric conducting portion 23 (the first electrode portion 25) when the first jaw obliquely facing surface (abutting portion) 143A of the pad member (insulating abutting member) 95 is in abutment with the probe electric conducting portion 23 (the probe obliquely facing surface 103A).

As shown in FIG. 19, in the first treatment mode, an ultrasonic generating current is output from the ultrasonic generating current supplier 8. Thus, the ultrasonic vibration is generated in the ultrasonic vibrator 12, and transmitted to the probe electric conducting portion 23 (the distal portion of the probe unit 3). In the first treatment mode, a high-frequency current is output from the high-frequency current supplier 9. Thus, the high-frequency current is transmitted to the probe electric conducting portion 23, and the probe electric conducting portion 23 has the first electric potential E1. The high-frequency current is also transmitted to the jaw electric conducting portion 93 of the jaw 42, and the jaw electric conducting portion 93 serves as a second electrode portion 105 having the second electric potential E2. In this case, no high-frequency current is transmitted to the movable plate 131, and the movement electric conducting portion 141 therefore does not function as an electrode.

Consequently, in the first treatment mode, the probe electric conducting portion 23 alone functions as the first electrode portion 25 having the first electric potential E1. In the first treatment mode, the distance between the probe electric conducting portion 23 (the probe perpendicularly facing surface 102) of the first electrode portion 25 and the jaw electric conducting portion 93 (the jaw perpendicularly facing surface 142) of the second electrode portion 105 is a first distance D1.

As shown in FIG. 22, in the second treatment mode, the surgeon presses the movement operation button 133 toward the inner peripheral direction, and the movement operation button 133 is thereby moved to the second operation position from the first operation position. As a result, the plate-side inclined surface 137A of the intermediary portion 132 slides on the sheath-side inclined surface 137B of the inner tube 75. Thus, the movable plate 131 moves toward the distal direction against the urging from the spring member 139. Here, when the movement operation button 133 is located at the second operation position, the movable plate 131 contacts the probe body 21. Therefore, the movable plate 131 is electrically connected to the probe body 21, and the high-frequency current is transmitted to the movable plate 131 from the probe body 21. When the high-frequency current is transmitted to the movable plate 131, the movement electric conducting portion 141 has the first electric potential E1.

As shown in FIG. 20, in the second treatment mode, the movement electric conducting portion 141 is located between the jaw perpendicularly facing surface 142 (the jaw 42) and the probe perpendicularly facing surface 102 (the probe electric conducting portion 23) in the opening-and-closing directions of the jaw 42 by the operation to move the movement operation button 133 to the second operation position. The movement electric conducting portion 141 includes a movable portion facing surface 145 perpendicular to the opening-and-closing directions of the jaw 42. In the second treatment mode in which the movement operation button 133 is located at the second operation position, the movable portion facing surface 145 is parallel to the jaw perpendicularly facing surface 142, and faces the jaw perpendicularly facing surface 142. The distance between the movable portion facing surface 145 (the movement electric conducting portion 141) and the jaw perpendicularly facing surface 142 (the second electrode portion 105) is the second distance D2 smaller than the first distance D1.

In the second treatment mode, no ultrasonic generating current is output from the ultrasonic generating current supplier 8, and a high-frequency current is output from the high-frequency current supplier 9 alone. Thus, no ultrasonic vibration is generated in the ultrasonic vibrator 12. The high-frequency current is transmitted to the probe electric conducting portion 23, and the probe electric conducting portion 23 has the first electric potential E1. The high-frequency current is also transmitted to the jaw electric conducting portion 93 of the jaw 42, and the jaw electric conducting portion 93 serves as the second electrode portion 105 having the second electric potential E2. At the same time, the high-frequency current is transmitted to the movable plate (movable portion) 131 from the probe body 21, so that the movement electric conducting portion 141 also has the first electric potential E1.

Therefore, in the second treatment mode, the probe electric conducting portion 23 and the movement electric conducting portion 141 function as the first electrode portion 25 having the first electric potential E1, and the movement electric conducting portion 141 serves as a part of the first electrode portion 25. Thus, in the second treatment mode, the distance between the movement electric conducting portion 141 (the movable portion facing surface 145) of the first electrode portion 25 and the jaw electric conducting portion 93 (the jaw perpendicularly facing surface 142) of the second electrode portion 105 is the second distance D2 smaller than the first distance D1.

As described above, the movement operation button (movement operation input portion) 133 serves as an inter-electrode distance changing unit configured to change the inter-electrode distance so that the second distance D2 between the first electrode portion 25 and the second electrode portion 105 in the second treatment mode is smaller than the first distance D1 between the first electrode portion 25 and the second electrode portion 105 in the first treatment mode. In the second treatment mode, no ultrasonic vibration is transmitted to the probe electric conducting portion 23 and the movement electric conducting portion 141 (the distal portion of the probe unit 3), and a high-frequency current alone is transmitted to the first electrode portion 25 and the second electrode portion 105.

Now, the functions of the grasping treatment device 1 according to the present embodiment are described. When the grasping treatment device 1 is used to conduct a treatment in the first treatment mode, the surgeon moves the movement operation button 133 which is the movement operation input portion to the first operation position. As a result, the movement electric conducting portion 141 is accommodated (housed) in the sheath body 41, and located to the proximal direction side of the jaw 42. In this state, the movable handle 33 is closed relative to the fixed handle 32. Thus, as has been described in the first embodiment, the jaw 42 is closed relative to the probe electric conducting portion 23 of the probe body 21 (the probe unit 3), and a grasping target such as a blood vessel is grasped between the jaw 42 and the probe electric conducting portion 23.

The surgeon then presses a treatment mode input button 57A which is the treatment mode input portion, and a switch portion 58A is turned on (closed). As a result, an ultrasonic generating current is output from the ultrasonic generating current supplier 8, and a high-frequency current is output from the high-frequency current supplier 9. The ultrasonic vibration is then generated in the ultrasonic vibrator 12, and the ultrasonic vibration is transmitted to the probe electric conducting portion 23 (the distal portion of the probe unit 3). The grasping target grasped between the probe electric conducting portion 23 (the distal portion of the probe unit 3) and the jaw 42 is cut and coagulated by frictional heat generated by the ultrasonic vibration of the probe unit 3.

The high-frequency current output from the high-frequency current supplier 9 is transmitted to the probe electric conducting portion 23 through the electric signal line 17, the ultrasonic vibrator 12, the horn 15, and the probe body 21 (the probe unit 3). When the high-frequency current is transmitted to the probe electric conducting portion 23, the probe electric conducting portion 23 has the first electric potential E1. A high-frequency current is also transmitted to the jaw electric conducting portion 93 from the high-frequency current supplier 9 through the electric signal line 69, the fourth electric conducting portion 63D, the movable cylindrical member 46, the inner pipe 77, and the jaw 42. When the high-frequency current is transmitted to the jaw electric conducting portion 93, the jaw electric conducting portion 93 functions as the second electrode portion 105 having the second electric potential E2 different in intensity from the first electric potential E1.

When the movement operation lever 83 is located at the first operation position, the movable plate 131 is electrically insulated from the probe body 21. Thus, no high-frequency current is transmitted to the movable plate 131, and the movement electric conducting portion 141 does not function as an electrode. Therefore, in the first treatment mode, the probe electric conducting portion 23 alone functions as the first electrode portion 25 having the first electric potential E1. The probe electric conducting portion 23 (the first electrode portion 25) has the first electric potential E1, and the jaw electric conducting portion 93 (the second electrode portion 105) has the second electric potential E2, so that a high-frequency current runs through the grasping target grasped between the probe electric conducting portion 23 and the jaw 42. Consequently, a grasping target such as the living tissue T is reformed, and the coagulation is accelerated.

When the grasping treatment device 1 is used to conduct a treatment in the second treatment mode, the surgeon moves the movement operation button 133 which is the movement operation input portion to the second operation position. As a result, the movement electric conducting portion 141 is located between the jaw perpendicularly facing surface 142 (the jaw 42) and the probe perpendicularly facing surface 102 (the probe electric conducting portion 23) in the opening-and-closing directions of the jaw 42.

In this state, the movable handle 33 is closed relative to the fixed handle 32. Thus, as has been described in the first embodiment, the jaw 42 is closed relative to the probe electric conducting portion 23 of the probe body 21 (the probe unit 3), and a grasping target such as a blood vessel is grasped between the movement electric conducting portion 141 and the jaw electric conducting portion 93 (the second electrode portion 105). At the same time, the grasping target is held between the movement electric conducting portion 141 and the jaw electric conducting portion 93 (the second electrode portion 105), and the grasping target is grasped.

The surgeon then presses a treatment mode input button 57B which is the second treatment mode input portion, and a switch portion 58B is turned on (closed). As a result, a high-frequency current is output from the high-frequency current supplier 9. In this case, no current is output from the ultrasonic generating current supplier 8. The high-frequency current output from the high-frequency current supplier 9 is transmitted to the probe electric conducting portion 23 through the electric signal line 17, the ultrasonic vibrator 12, the horn 15, and the probe body 21 (the probe unit 3). When the high-frequency current is transmitted to the probe electric conducting portion 23, the probe electric conducting portion 23 has the first electric potential E1. A high-frequency current is also transmitted to the jaw electric conducting portion 93 from the high-frequency current supplier 9 through the electric signal line 69, the fourth electric conducting portion 63D, the movable cylindrical member 46, the inner pipe 77, and the jaw 42. When the high-frequency current is transmitted to the jaw electric conducting portion 93, the jaw electric conducting portion 93 functions as the second electrode portion 105 having the second electric potential E2 different in intensity from the first electric potential E1.

When the movement operation button 133 is located at the second operation position, the movable plate 131 is electrically connected to the probe body 21. Thus, a high-frequency current is transmitted to the movable plate 131, and the movement electric conducting portion 141 functions as the first electrode portion 25 having the first electric potential E1. Therefore, in the second treatment mode, the probe electric conducting portion 23 and the movement electric conducting portion 141 function as the first electrode portion 25 having the first electric potential E1, and the movement electric conducting portion 141 serves as a part of the first electrode portion 25. In the second treatment mode, no ultrasonic vibration is transmitted to the probe electric conducting portion 23 and the movement electric conducting portion 141 (the distal portion of the probe unit 3), and a high-frequency current alone is transmitted to the first electrode portion 25 and the second electrode portion 105.

The first electrode portion 25 (the probe electric conducting portion 23 and the movement electric conducting portion 141) has the first electric potential E1, and the second electrode portion 105 (the jaw electric conducting portion 93) has the second electric potential E2, so that a high-frequency current also runs through the grasping target grasped between the movement electric conducting portion 141 and the jaw 42. Consequently, a grasping target such as the living tissue T is reformed and coagulated.

In the second treatment mode, the movement electric conducting portion 141 is located between the jaw 42 and the probe electric conducting portion 23 in the opening-and-closing directions of the jaw 42. Therefore, the distance between the movement electric conducting portion 141 (the movable portion facing surface 145) of the first electrode portion 25 and the jaw electric conducting portion 93 (the jaw perpendicularly facing surface 142) of the second electrode portion 105 is the second distance D2. The second distance D2 is smaller than the first distance D1. That is, the distance between the first electrode portion 25 and the second electrode portion 105 is smaller in the second treatment mode than in the first treatment mode. Since the distance between the first electrode portion 25 and the second electrode portion 105 is smaller, the reformation of the living tissue T (grasping target) with the high-frequency current is more accelerated in the second treatment mode than in the first treatment mode. Therefore, the performance of the coagulation of the grasping target with the high-frequency current is improved, so that the deterioration in the performance of the coagulation of the grasping target is prevented in the second treatment mode, which does not use the ultrasonic vibration. Consequently, the grasping target (living tissue) is stably sealed in the second treatment mode, which does not use the ultrasonic vibration.

In the second treatment mode, the movement electric conducting portion 141 is located between the jaw perpendicularly facing surface 142 (the jaw electric conducting portion 93) and the probe perpendicularly facing surface 102 in the opening-and-closing directions of the jaw 42. The grasping target is grasped between the movement electric conducting portion 141 and the jaw 42 (the second electrode portion 105). The jaw perpendicularly facing surface 142 of the jaw electric conducting portion 93 is perpendicular to the opening-and-closing directions of the jaw 42. The movable portion facing surface 145 of the movement electric conducting portion 141 is parallel to the jaw perpendicularly facing surface 142, and faces the jaw perpendicularly facing surface 142. Since the jaw perpendicularly facing surface 142 and the movable portion facing surface 145 are perpendicular to the opening-and-closing directions of the jaw 42, the grasping force to grasp the grasping target between the movement electric conducting portion 141 and the jaw electric conducting portion 93 (the second electrode portion 105) is greater. The greater grasping force further improves the performance of the coagulation of the grasping target with the high-frequency current. Consequently, the grasping target (living tissue) is more stably sealed.

Accordingly, the grasping treatment device 1 having the configuration described above has the following advantageous effects. In the grasping treatment device 1, in the second treatment mode, the movement electric conducting portion 141 is located between the jaw 42 and the probe electric conducting portion 23 in the opening-and-closing directions of the jaw 42. Thus, the distance between the movement electric conducting portion 141 (the movable portion facing surface 145) of the first electrode portion 25 and the jaw electric conducting portion 93 (the jaw perpendicularly facing surface 142) of the second electrode portion 105 is the second distance D2. The second distance D2 is smaller than the first distance D1. That is, the distance between the first electrode portion 25 and the second electrode portion 105 is smaller in the second treatment mode than in the first treatment mode. Since the distance between the first electrode portion 25 and the second electrode portion 105 is smaller, the reformation of the living tissue T (grasping target) with the high-frequency current is more accelerated in the second treatment mode than in the first treatment mode. Therefore, the performance of the coagulation of the grasping target with the high-frequency current is improved, so that the deterioration in the performance of the coagulation of the grasping target can be prevented in the second treatment mode, which does not use the ultrasonic vibration. Consequently, the grasping target (living tissue) can be stably sealed in the second treatment mode, which does not use the ultrasonic vibration.

(Modification of Second Embodiment)

Figure 23:
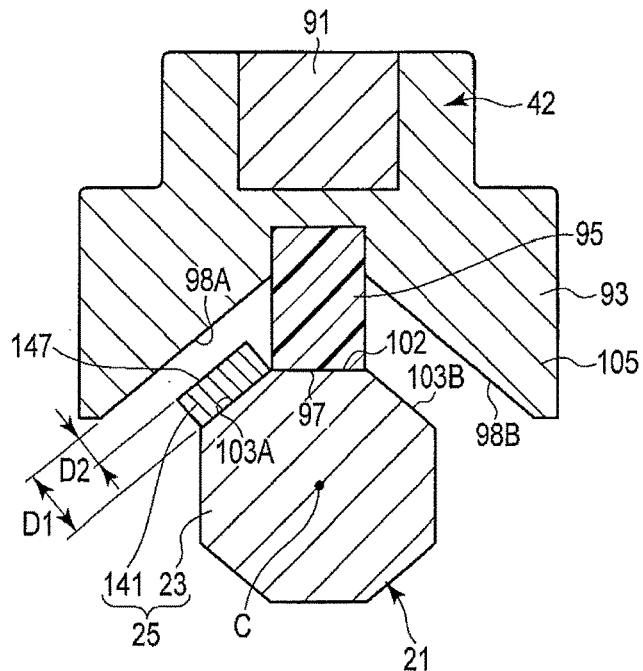
FIG. 23 is a schematic sectional view showing configurations of a distal portion of a probe unit, a distal portion of a sheath unit, and a jaw according to a modification of the second embodiment in the second treatment mode.

According to the second embodiment, in the second treatment mode, the movement electric conducting portion 141 is located between the jaw perpendicularly facing surface 142 (the jaw electric conducting portion 93) and the probe perpendicularly facing surface 102 in the opening-and-closing directions of the jaw 42, and the movable portion facing surface 145 of the movement electric conducting portion 141 is perpendicular to the opening-and-closing directions of the jaw 42. However, the present invention is not limited to this. For example, a configuration shown as a modification in FIG. 23 may be applied. In FIG. 23, the grasping target T grasped between the jaw 42 and the probe body 21 (the probe electric conducting portion 23) is not shown.

As shown in FIG. 23, in the present modification, the jaw 42 has a configuration similar to that in the first embodiment, and includes a jaw perpendicularly facing surface 97, and jaw obliquely facing surfaces 98A and 98B. That is, the positional relation between the jaw electric conducting portion 93 and the pad member (insulating abutting member) 95 is similar to that in the first embodiment.

In the second treatment mode, the movement electric conducting portion 141 is provided between the jaw obliquely facing surface 98A and the probe obliquely facing surface 103A in the opening-and-closing directions of the jaw 42. In the present modification, the movement electric conducting portion 141 includes a movable portion facing surface 147 substantially parallel to the jaw obliquely facing surface 98A and the probe obliquely facing surface 103A. The movable portion facing surface 147 is not perpendicular to the opening-and-closing directions of the jaw 42, and faces the jaw obliquely facing surface 98A in the second treatment mode.

In the present modification as well, the movement electric conducting portion 141 is located to the proximal direction side of the jaw 42 in the first treatment mode. Thus, the distance between the probe obliquely facing surface 103A and the jaw obliquely facing surface 98A (the distance between the probe obliquely facing surface 103B and the jaw obliquely facing surface 98B) is the first distance D1 between the first electrode portion 25 (the probe electric conducting portion 23) and the second electrode portion 105 (the jaw electric conducting portion 93) in the first treatment mode. In the second treatment mode, the movement electric conducting portion 141 is located between the jaw obliquely facing surface 98A and the probe obliquely facing surface 103A in the opening-and-closing directions of the jaw 42. Thus, the distance between the movable portion facing surface 147 and the jaw obliquely facing surface 98A is the second distance D2 between the first electrode portion 25 (the movement electric conducting portion 141) and the second electrode portion 105 (the jaw electric conducting portion 93) in the second treatment mode.

As described above, in the present modification as well, the distance between the first electrode portion 25 and the second electrode portion 105 is smaller in the second treatment mode than in the first treatment mode. Since the distance between the first electrode portion 25 and the second electrode portion 105 is smaller, the reformation of the living tissue T (grasping target) with the high-frequency current is more accelerated in the second treatment mode than in the first treatment mode. However, in the present modification, the movable portion facing surface 145 perpendicular to the opening-and-closing directions of the jaw 42 is not provided in the movement electric conducting portion 141, in contrast with the first embodiment. Thus, the grasping force to grasp the grasping target in the second treatment mode is lower than in the second embodiment.

As described above, according to the modification, the configuration which allows the distance between the first electrode portion 25 and the second electrode portion 105 to be smaller in the second treatment mode than in the first treatment mode is not limited to the second embodiment. That is, the movable portion (the movable plate 131) provided in the probe unit 3 has only to be movable relative to the probe body 21 and the sheath body 41 along the longitudinal axis C. The movement electric conducting portion 141 has only to be provided in the distal portion of the movable portion (the movable plate 131), and the movement operation input portion (the movement operation button 133) to which an operation of moving the movable portion is input has only to be provided. In this case, in the first treatment mode, the movement electric conducting portion 141 is located to the proximal direction side of the jaw 42 by the operation in the movement operation input portion. In the second treatment mode, the movement electric conducting portion 141 is located between the jaw 42 and the probe electric conducting portion 23 in the opening-and-closing directions of the jaw 42 by the operation in the movement operation input portion. Moreover, in the second treatment mode, the high-frequency current is transmitted through the movable portion (the movable plate 131), and the movement electric conducting portion 141 functions as at least a part of the first electrode portion 25.

(Third Embodiment)

Now, a third embodiment of the present invention is described with reference to FIG. 24 to FIG. 30. In the third embodiment, the configuration according to the first embodiment is modified as below. The same parts as those in the first embodiment are provided with the same reference signs, and are not described.

Figure 24:
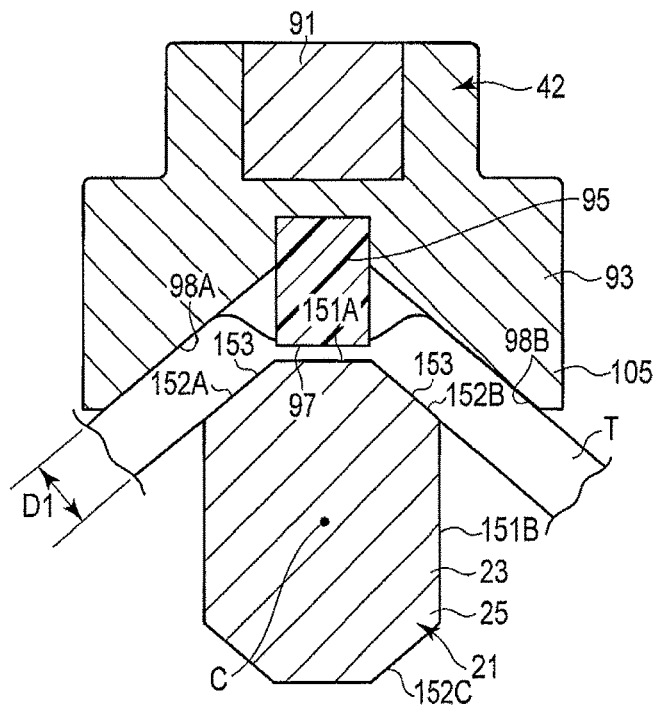
FIG. 24 is a schematic sectional view showing configurations of a distal portion of a probe unit and a jaw according to a third embodiment of the present invention in the first treatment mode.

FIG. 24 and FIG. 25 are diagrams showing the configurations of the distal portion of a probe unit 3 and a jaw 42. FIG. 24 shows a first treatment mode. FIG. 25 shows a second treatment mode. As shown in FIG. 24 and FIG. 25, in the present embodiment, no movable portion (movable plate 81, 131) is provided, in contrast with the first embodiment and the second embodiment. Therefore, when a high-frequency current is transmitted through a probe body 21 (the probe unit 3), a probe electric conducting portion 23 alone functions as a first electrode portion 25 having a first electric potential E1. When a high-frequency current is transmitted through a sheath body 41 (a sheath unit 5), a jaw electric conducting portion 93 alone functions as a second electrode portion 105 having a second electric potential E2. The jaw 42 has a configuration similar to that in the first embodiment, and includes a jaw perpendicularly facing surface 97, and jaw obliquely facing surfaces 98A and 98B.

As shown in FIG. 24, the probe electric conducting portion 23 includes a first probe perpendicularly facing surface 151A, and a second probe perpendicularly facing surface 151B provided apart from the first probe perpendicularly facing surface 151A by an angular position of about 90° in one of the directions around the longitudinal axis. In the first treatment mode, the first probe perpendicularly facing surface 151A is located perpendicularly to the opening-and-closing directions of the jaw 42 (i.e., parallel to the jaw perpendicularly facing surface 97). In the first treatment mode, the jaw perpendicularly facing surface (abutting portion) 97 of a pad member 95 can abut on the first probe perpendicularly facing surface 151A.

In the first treatment mode, a first probe obliquely facing surface 152A is provided on one side of the first probe perpendicularly facing surface 151A in width directions which are directions perpendicular to the longitudinal axis C and perpendicular to the opening-and-closing directions of the jaw 42. A second probe obliquely facing surface 152B is provided on the other side of the first probe perpendicularly facing surface 151A in the width directions. The second probe obliquely facing surface 152B is provided between the first probe perpendicularly facing surface 151A and the second probe perpendicularly facing surface 151B. The second probe obliquely facing surface 152B is provided apart from the first probe obliquely facing surface 152A by an angular position of about 90° in one of the directions around the longitudinal axis.

In the first treatment mode, the first probe obliquely facing surface 152A is substantially parallel to the jaw obliquely facing surface 98A, and faces the jaw obliquely facing surface 98A. The second probe obliquely facing surface 152B is substantially parallel to the jaw obliquely facing surface 98B, and faces the jaw obliquely facing surface 98B. That is, a first electrode facing surface 153 which faces the jaw electric conducting portion 93 in the first treatment mode is formed by the first probe obliquely facing surface 152A and the second probe obliquely facing surface 152B.

When the jaw perpendicularly facing surface (abutting portion) 97 is in abutment with the first probe perpendicularly facing surface 151A (the probe electric conducting portion 23), a clearance is formed between the first electrode facing surface 153 (the first electrode portion 25) and the jaw electric conducting portion 93 (the second electrode portion 105). In the first treatment mode, the distance between the first electrode facing surface 153 (the first probe obliquely facing surface 152A and the second probe obliquely facing surface 152B) of the first electrode portion 25 and the jaw electric conducting portion 93 (the jaw obliquely facing surfaces 98A and 98B) of the second electrode portion 105 is a first distance D1. Therefore, the first electrode facing surface 153 faces the jaw electric conducting portion 93 with being spaced by the first distance D1.

As shown in FIG. 25, in the second treatment mode, the probe electric conducting portion 23 (the probe unit 3) is located to be rotated relative to the jaw 42 and the sheath unit 5 by a rotation angle of about 90° in one of the directions around the longitudinal axis from the first treatment mode. Thus, in the second treatment mode, the second probe perpendicularly facing surface 151B is located perpendicularly to the opening-and-closing directions of the jaw 42 (i.e., parallel to the jaw perpendicularly facing surface 97). In the second treatment mode, the jaw perpendicularly facing surface (abutting portion) 97 of the pad member 95 can abut on the second probe perpendicularly facing surface 151B.

In the second treatment mode, the second probe obliquely facing surface 152B is provided on one side of the second probe perpendicularly facing surface 151B in the width directions which are the directions perpendicular to the longitudinal axis C and perpendicular to the opening-and-closing directions of the jaw 42. A third probe obliquely facing surface 152C is provided on the other side of the second probe perpendicularly facing surface 151B in the width directions. The third probe obliquely facing surface 152C is provided apart from the second probe obliquely facing surface 152B by an angular position of about 90° in one of the directions around the longitudinal axis, and apart from the first probe obliquely facing surface 152A by an angular position of about 180° in one of the directions around the longitudinal axis.

In the second treatment mode, the second probe obliquely facing surface 152B is substantially parallel to the jaw obliquely facing surface 98A, and faces the jaw obliquely facing surface 98A. The third probe obliquely facing surface 152C is substantially parallel to the jaw obliquely facing surface 98B, and faces the jaw obliquely facing surface 98B. That is, a second electrode facing surface 155 which faces the jaw electric conducting portion 93 in the second treatment mode is formed by the second probe obliquely facing surface 152B and the third probe obliquely facing surface 152C. Since the probe obliquely facing surfaces 152A to 152C are arranged as described above, the second electrode facing surface 155 is located apart from the first electrode facing surface 153 by an angular position of about 90° in one of the directions around the longitudinal axis.

When the jaw perpendicularly facing surface (abutting portion) 97 is in abutment with the second probe perpendicularly facing surface 151B (the probe electric conducting portion 23), a clearance is formed between the second electrode facing surface 155 (the first electrode portion 25) and the jaw electric conducting portion 93 (the second electrode portion 105). In the second treatment mode, the distance between the second electrode facing surface 155 (the second probe obliquely facing surface 152B and the third probe obliquely facing surface 152C) of the first electrode portion 25 and the jaw electric conducting portion 93 (the jaw obliquely facing surfaces 98A and 98B) of the second electrode portion 105 is a second distance D2 smaller than the first distance D1. Therefore, the second electrode facing surface 155 faces the jaw electric conducting portion 93 with being spaced by the second distance D2 smaller than the first distance D1.

Figure 26:
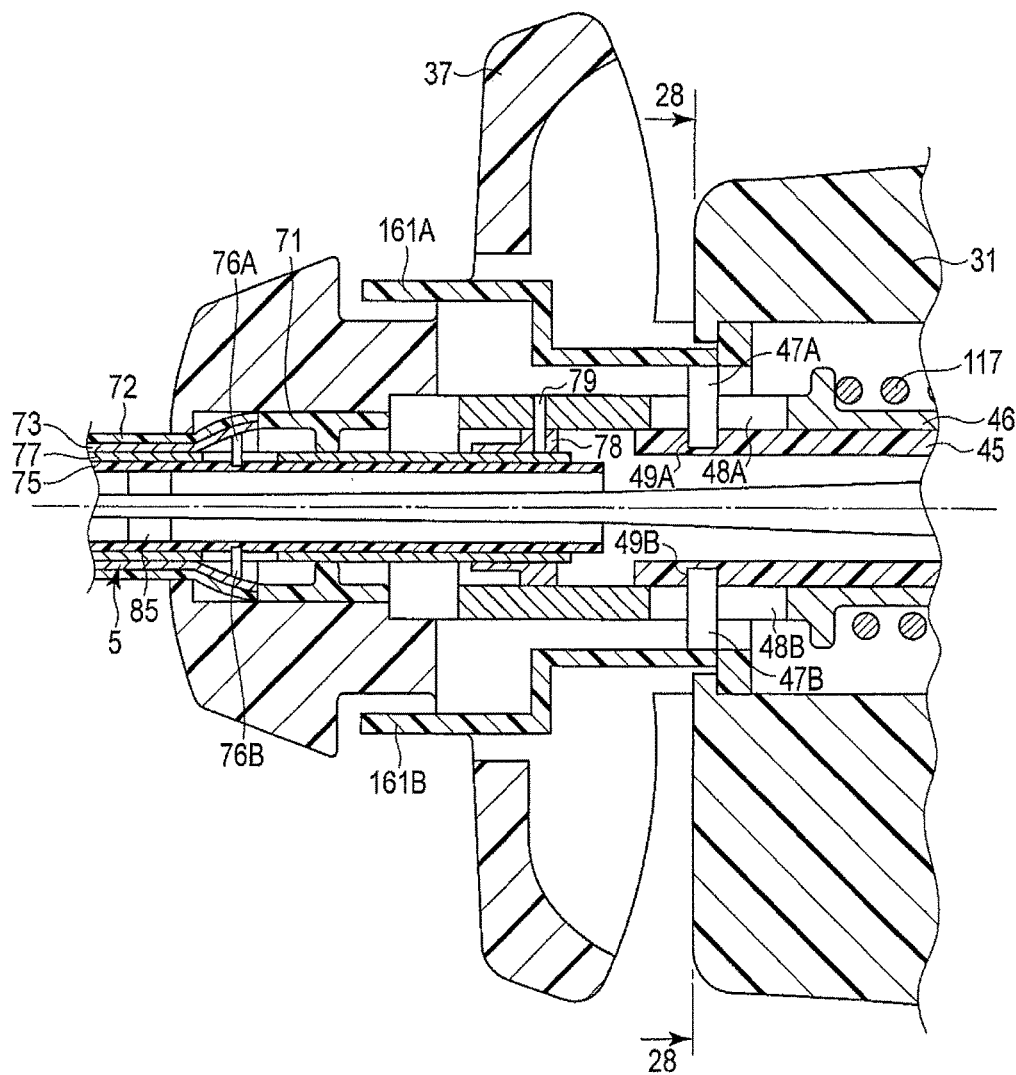
FIG. 26 is a schematic sectional view showing an internal configuration of a rotational operation knob according the third embodiment in the first treatment mode and in a relative rotation regulated state.
Figure 27:
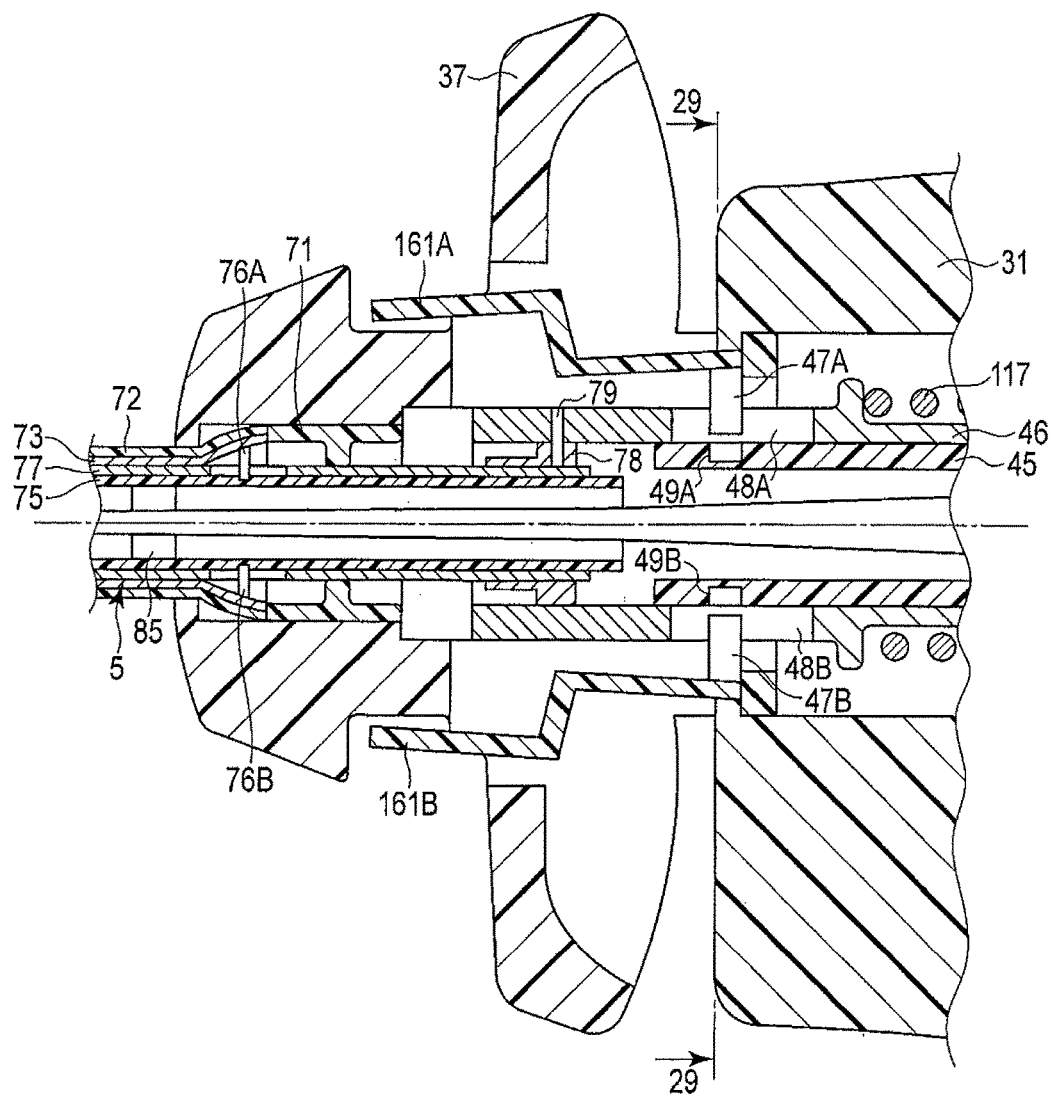
FIG. 27 is a schematic sectional view showing the internal configuration of a rotational operation knob according the third embodiment in a relative rotation allowed state.
Figure 28:
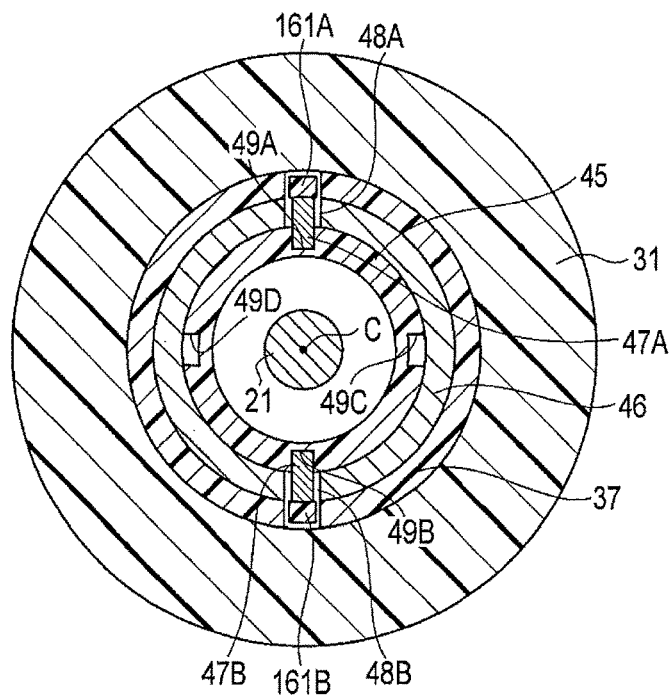
FIG. 28 is a sectional view taken along the line 28-28 in FIG. 26.
Figure 29:
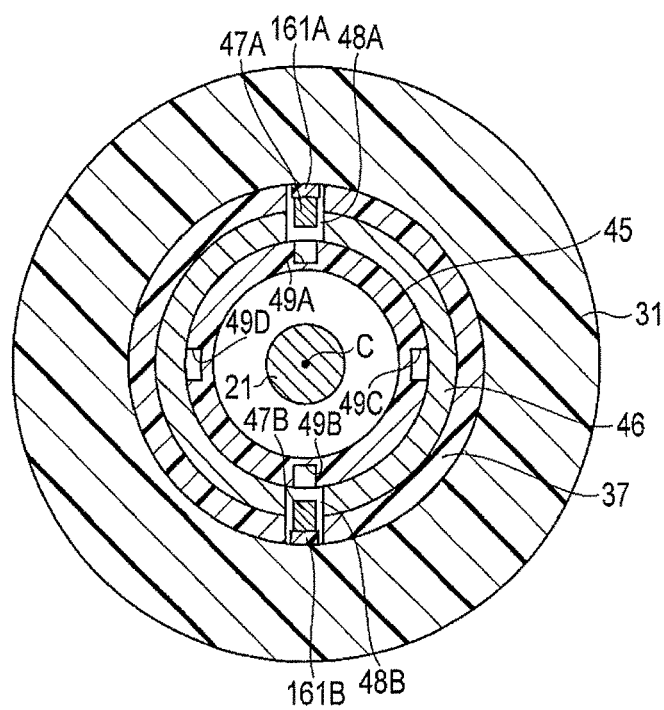
FIG. 29 is a sectional view taken along the line 29-29 in FIG. 27.

FIG. 26 and FIG. 27 are diagrams showing an internal configuration of a rotational operation knob 37. FIG. 28 is a sectional view taken along the line 28-28 in FIG. 26. FIG. 29 is a sectional view taken along the line 29-29 in FIG. 27. FIG. 26 and FIG. 28 show a configuration in the first treatment mode and in a relative rotation regulated state in which the probe unit 3 and the sheath unit 5 are unrotatable relative to each other in the directions around the longitudinal axis.

As shown in FIG. 26 and FIG. 28, in the present embodiment, engaging pins 47A and 47B are provided, as in the first embodiment. Through-holes 48A and 48B are provided in a movable cylindrical member 46, and engaging depressions 49A and 49B are provided in a connection cylindrical member 45. Two engaging depressions, 49C and 49D, are further provided in the connection cylindrical member 45 in addition to the engaging depressions 49A and 49B. The engaging depressions 49C and 49D are provided apart from each other by an angular position of about 180° in the directions around the longitudinal axis. Each of the engaging depressions 49C and 49D is provided about 90° apart from the engaging depression 49A in the directions around the longitudinal axis.

The engaging pin 47A is fixed to a rotation state switch lever 161A which is a rotation state switch portion. The engaging pin 47B is fixed to a rotation state switch lever 161B which is a rotation state switch portion. The rotation state switch levers 161A and 161B are located apart from each other in the directions around the longitudinal axis. Each of the rotation state switch levers 161A and 161B is movably attached to the rotational operation knob 37 between a first operation position and a second operation position in accordance with the operation by the surgeon (operator).

In the first treatment mode and in the relative rotation regulated state, each of the rotation state switch levers 161A and 161B is located at the first operation position. At the same time, the engaging pin 47A is inserted through the through-hole 48A, and engaged with the engaging depression 49A. The engaging pin 47B is inserted through the through-hole 48B, and engaged with the engaging depression 49B. When each of the engaging pins 47A and 47B is engaged with the corresponding engaging depression 49A or 49B, the connection cylindrical member 45 is fixed to the rotational operation knob 37. When each of the engaging pins 47A and 47B is inserted through the corresponding through-hole 48A or 48B, the movable cylindrical member 46 and the rotational operation knob 37 regulated unrotatably relative to each other in the directions around the longitudinal axis. The configuration described above allows the connection cylindrical member 45 and the movable cylindrical member 46 (the sheath unit 5 and the jaw 42) to be rotatable relative to the cylindrical case 31 together with the rotational operation knob 37 in the directions around the longitudinal axis.

When the rotational operation knob 37 is rotated in one of the directions around the longitudinal axis, a rotational drive force from the rotational operation knob 37 is transmitted to the probe body 21 (the probe unit 3) via the connection cylindrical member 45 and the elastic member 51. Consequently, the probe unit 3 can rotate relative to the cylindrical case 31 together with the rotational operation knob 37 and the connection cylindrical member 45. As described above, in the relative rotation regulated state, an operation of rotating the probe unit 3, the sheath unit 5, and the jaw 42 in one of the directions around the longitudinal axis is input by the rotational operation knob 37 which is the rotational operation input portion. That is, in the relative rotation regulated state, the sheath unit 5 and the probe unit 3 are unrotatable relative to each other in the directions around the longitudinal axis.

FIG. 27 and FIG. 29 show a relative rotation allowed state in which the sheath unit 5 and the probe unit 3 are rotatable relative to each other in the directions around the longitudinal axis. In the relative rotation allowed state, each of the rotation state switch levers 161A and 161B is moved to the second operation position from the first operation position in accordance with the operation by the surgeon (operator). At the same time, the engaging pin 47A is inserted into the through-hole 48A, but is not engaged with any of the engaging depressions 49A to 49D. The engaging pin 47B is inserted into the through-hole 48B, but is not engaged with any of the engaging depressions 49A to 49D. Since each of the engaging pins 47A and 47B is not engaged with any of the engaging depressions 49A to 49D, the connection cylindrical member 45 is not fixed to the rotational operation knob 37. Therefore, the connection cylindrical member 45 and the rotational operation knob 37 are rotatable relative to each other in the directions around the longitudinal axis.

In the meantime, each of the engaging pins 47A and 47B is inserted into the corresponding through-hole 48A or 48B. Thus, the movable cylindrical member 46 and the rotational operation knob 37 are regulated unrotatably relative to each other in the directions around the longitudinal axis. Therefore, the movable cylindrical member 46 (the sheath unit 5 and the jaw 42) are rotatable relative to the cylindrical case 31 together with the rotational operation knob 37 in the directions around the longitudinal axis.

In the relative rotation allowed state, the connection cylindrical member 45 is not fixed to the rotational operation knob 37. Thus, when the rotational operation knob 37 is rotated in one of the directions around the longitudinal axis, the rotational drive force from the rotational operation knob 37 is not transmitted to the connection cylindrical member 45. Therefore, the rotational operation of the rotational operation knob 37 is not transmitted to the probe body 21 (the probe unit 3) fixed to the connection cylindrical member 45. That is, the probe unit 3 and the rotational operation knob 37 are rotatable relative to each other in the directions around the longitudinal axis.

As described above, in the relative rotation allowed state, an operation of rotating the sheath unit 5 and the jaw 42 relative to the probe unit 3 in one of the directions around the longitudinal axis is input by the rotational operation knob 37 which is the rotational operation input portion. That is, in the relative rotation allowed state, the sheath unit 5 and the probe unit 3 are rotatable relative to each other in the directions around the longitudinal axis.

Figure 30:
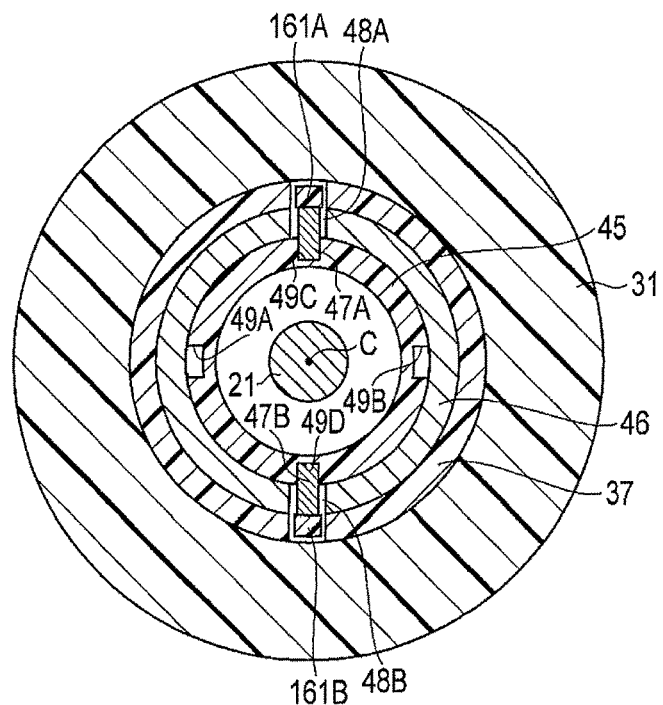
FIG. 30 is a schematic sectional view showing the linkage (coupling part) of the rotational operation knob, a sheath unit, and a connection cylindrical member according the third embodiment in the second treatment mode and in the relative rotation regulated state.

FIG. 30 is a diagram showing the coupling part (linkage) of the rotational operation knob 37, the sheath unit 5, and the connection cylindrical member 45 in the second treatment mode. As shown in FIG. 30, in the second treatment mode, the connection cylindrical member 45 is located to be rotated relative to the rotational operation knob 37 and the movable cylindrical member 46 (the sheath unit 5) by a rotation angle of about 90° in one of the directions around the longitudinal axis from the first treatment mode. At the same time, the probe unit 3 and the sheath unit 5 are in the relative rotation regulated state to be unrotatable relative to each other in the directions around the longitudinal axis.

In the second treatment mode and in the relative rotation regulated state, each of the rotation state switch levers 161A and 161B is located at the first operation position. At the same time, as in the first treatment mode, the engaging pin 47A is inserted through the through-hole 48A, and the engaging pin 47B is inserted through the through-hole 48B. However, in contrast with the first treatment mode, the engaging pin 47A is engaged with the engaging depression 49C, and the engaging pin 47B is engaged with the engaging depression 49D. Thus, the connection cylindrical member 45 is fixed to the rotational operation knob 37 in a position in which the connection cylindrical member 45 is rotated relative to the rotational operation knob 37 and the sheath unit 5 by a rotation angle of about 90° in one of the directions around the longitudinal axis from the first treatment mode.

The probe body 21 (the probe unit 3) is fixed to the connection cylindrical member 45 via the elastic member 51 both in the relative rotation regulated state and the relative rotation allowed state. Therefore, in the second treatment mode, the probe unit 3 is rotated relative to the rotational operation knob 37 and the sheath unit 5 by a rotation angle of about 90° in one of the directions around the longitudinal axis from the first treatment mode. Thus, in the second treatment mode, the probe electric conducting portion 23 is located to be a position in which the probe electric conducting portion 23 is rotated relative to the jaw 42 and the sheath unit 5 by a rotation angle of about 90° in one of the directions around the longitudinal axis from the first treatment mode (see FIG. 24 and FIG. 25).

As described above, the rotation state switch levers (rotation state switch portions) 161A and 161B and the rotational operation knob (rotational operation input portion) 37 serve as an inter-electrode distance changing unit configured to change an inter-electrode distance so that the second distance D2 between the first electrode portion 25 and the second electrode portion 105 in the second treatment mode is smaller than the first distance D1 between the first electrode portion 25 and the second electrode portion 105 in the first treatment mode. The angular positions of the probe unit 3 and the sheath unit 5 relative to each other in the directions around the longitudinal axis in the relative rotation allowed state may be changed by the operation in the rotational operation knob 37 as described above, and may be changed by direct rotation of the probe body 21 (the probe unit 3) in one of the directions around the longitudinal axis.

Now, the functions of the grasping treatment device 1 according to the present embodiment are described. When the grasping treatment device 1 is used to conduct a treatment in the first treatment mode, the rotation state switch levers 161A and 161B which are the rotation state switch portions are located at the first operation position. The engaging pin 47A is engaged with the engaging depression 49A, and the engaging pin 47B is engaged with the engaging depression 49B. Thus, the probe unit 3 and the sheath unit 5 are brought into the relative rotation regulated state to be unrotatable relative to each other in the directions around the longitudinal axis. In this state, the movable handle 33 is closed relative to the fixed handle 32. Thus, as has been described in the first embodiment, the jaw 42 is closed relative to the probe electric conducting portion 23 of the probe body 21 (the probe unit 3), and a grasping target such as a blood vessel is grasped between the jaw 42 and the probe electric conducting portion 23.

The surgeon then presses a treatment mode input button 57A which is a treatment mode input portion, and a switch portion 58A is turned on (closed). As a result, an ultrasonic generating current is output from an ultrasonic generating current supplier 8, and a high-frequency current is output from a high-frequency current supplier 9. The ultrasonic vibration is then generated in an ultrasonic vibrator 12, and the ultrasonic vibration is transmitted to the probe electric conducting portion 23 (the distal portion of the probe unit 3). The grasping target grasped between the probe electric conducting portion 23 (the distal portion of the probe body 21) and the jaw 42 is cut and coagulated by frictional heat generated by the ultrasonic vibration of the probe unit 3.

The high-frequency current output from the high-frequency current supplier 9 is transmitted to the probe electric conducting portion 23 through an electric signal line 17, the ultrasonic vibrator 12, a horn 15, and the probe body 21 (the probe unit 3). When the high-frequency current is transmitted to the probe electric conducting portion 23, the probe electric conducting portion 23 functions as the first electrode portion 25 having a first electric potential E1. A high-frequency current is also transmitted to the jaw electric conducting portion 93 from the high-frequency current supplier 9 through an electric signal line 69, a fourth electric conducting portion 63D, the movable cylindrical member 46, an inner pipe 77, and the jaw 42. When the high-frequency current is transmitted to the jaw electric conducting portion 93, the jaw electric conducting portion 93 functions as the second electrode portion 105 having the second electric potential E2 different in intensity from the first electric potential E1. The probe electric conducting portion 23 (the first electrode portion 25) has the first electric potential E1, and the jaw electric conducting portion 93 (the second electrode portion 105) has the second electric potential E2, so that a high-frequency current runs through the grasping target grasped between the probe electric conducting portion 23 and the jaw 42. Consequently, a grasping target such as the living tissue T is reformed, and the coagulation is accelerated.

When a treatment is conducted in the second treatment mode after the treatment in the first treatment mode, the operator moves the rotation state switch levers 161A and 161B which are the rotation state switch portions to the second operation position. As a result, the engaging pin 47A is disengaged from the engaging depression 49A, and the engaging pin 47B is disengaged from the engaging depression 49B. Therefore, the probe unit 3 and the sheath unit 5 are brought into the relative rotation allowed state to be rotatable relative to each other in the directions around the longitudinal axis.

In this state, an operation of rotating the sheath unit 5 and the jaw 42 relative to the probe unit 3 in one of the directions around the longitudinal axis is performed by the rotational operation knob 37 which is the rotational operation input portion. Instead of the operation in the rotational operation knob 37, an operation to directly rotate the probe unit 3 relative to the sheath unit 5 and the jaw 42 may be performed. The probe unit 3 is then located at an angular position which is rotated about 90° relative to the rotational operation knob 37 and the sheath unit 5 in one of the directions around the longitudinal axis from the first treatment mode.

The rotation state switch levers 161A and 161B are then moved to the first operation position. At the same time, the connection cylindrical member 45 is rotated relative to the rotational operation knob 37 by a rotation angle of about 90° in one of the directions around the longitudinal axis from the first treatment mode. Thus, the engaging pin 47A is engaged with the engaging depression 49C, and the engaging pin 47B is engaged with the engaging depression 49D. Thus, the probe unit 3 and the sheath unit 5 are brought into the relative rotation regulated state to be unrotatable relative to each other in the directions around the longitudinal axis.

The treatment in the second treatment mode is then conducted. When the treatment is conducted in the second treatment mode, the movable handle 33 is firstly closed relative to the fixed handle 32. Thus, as has been described in the first embodiment, the jaw 42 is closed relative to the probe electric conducting portion 23 of the probe body 21 (the probe unit 3), and a grasping target such as a blood vessel is grasped between the probe electric conducting portion 23 and the jaw electric conducting portion 93.

The surgeon then presses a treatment mode input button 57B which is a treatment mode input portion, and a switch portion 58B is turned on (closed). As a result, a high-frequency current is output from the high-frequency current supplier 9. In this case, no current is output from the ultrasonic generating current supplier 8. The high-frequency current output from the high-frequency current supplier 9 is transmitted to the probe electric conducting portion 23 through the electric signal line 17, the ultrasonic vibrator 12, the horn 15, and the probe body 21 (the probe unit 3). When the high-frequency current is transmitted to the probe electric conducting portion 23, the probe electric conducting portion 23 functions as the first electrode portion 25 having the first electric potential E1.

A high-frequency current is also transmitted to the jaw electric conducting portion 93 from the high-frequency current supplier 9 through the electric signal line 69, the fourth electric conducting portion 63D, the movable cylindrical member 46, the inner pipe 77, and the jaw 42. When the high-frequency current is transmitted to the jaw electric conducting portion 93, the jaw electric conducting portion 93 functions as the second electrode portion 105 having the second electric potential E2 different in intensity from the first electric potential E1. In the second treatment mode, no ultrasonic vibration is transmitted to the probe electric conducting portion 23 and the movement electric conducting portion 141 (the distal portion of the probe unit 3), and a high-frequency current alone is transmitted to the first electrode portion 25 and the second electrode portion 105. The first electrode portion 25 (the probe electric conducting portion 23) has the first electric potential E1, and the second electrode portion 105 (the jaw electric conducting portion 93) has the second electric potential E2, so that a high-frequency current runs through the grasping target grasped between the probe electric conducting portion 23 and the jaw 42. Consequently, a grasping target such as the living tissue T is reformed, and coagulated.

In the second treatment mode, the probe electric conducting portion 23 is located to be rotated relative to the jaw 42 and the sheath unit 5 by a rotation angle of about 90° in one of the directions around the longitudinal axis from the first treatment mode. Thus, the distance between the second electrode facing surface 155 (the second probe obliquely facing surface 152B and the third probe obliquely facing surface 152C) of the first electrode portion 25 and the jaw electric conducting portion 93 (the jaw obliquely facing surfaces 98A and 98B) of the second electrode portion 105 is a second distance D2. The second distance D2 is smaller than the first distance D1. That is, the distance between the first electrode portion 25 and the second electrode portion 105 is smaller in the second treatment mode than in the first treatment mode. Since the distance between the first electrode portion 25 and the second electrode portion 105 is smaller, the reformation of the living tissue T (grasping target) with the high-frequency current is more accelerated in the second treatment mode than in the first treatment mode. Therefore, the performance of the coagulation of the grasping target with the high-frequency current is improved, so that the deterioration in the performance of the coagulation of the grasping target is prevented in the second treatment mode, which does not use the ultrasonic vibration. Consequently, the grasping target (living tissue) is stably sealed in the second treatment mode, which does not use the ultrasonic vibration.

Accordingly, the grasping treatment device 1 having the configuration described above has the following advantageous effects. In the grasping treatment device 1, in the second treatment mode, the probe electric conducting portion 23 is located to be rotated relative to the jaw 42 and the sheath unit 5 by a rotation angle of about 90° in one of the directions around the longitudinal axis from the first treatment mode. Thus, the distance between the second electrode facing surface 155 (the second probe obliquely facing surface 152B and the third probe obliquely facing surface 152C) of the first electrode portion 25 and the jaw electric conducting portion 93 (the jaw obliquely facing surfaces 98A and 98B) of the second electrode portion 105 is a second distance D2. The second distance D2 is smaller than the first distance D1. That is, the distance between the first electrode portion 25 and the second electrode portion 105 is smaller in the second treatment mode than in the first treatment mode. Since the distance between the first electrode portion 25 and the second electrode portion 105 is smaller, the reformation of the living tissue T (grasping target) with the high-frequency current is more accelerated in the second treatment mode than in the first treatment mode. Therefore, the performance of the coagulation of the grasping target with the high-frequency current is improved, so that the deterioration in the performance of the coagulation of the grasping target is prevented in the second treatment mode, which does not use the ultrasonic vibration. Consequently, the grasping target (living tissue) can be stably sealed in the second treatment mode, which does not use the ultrasonic vibration.

(Modification of Third Embodiment)

Figure 31:
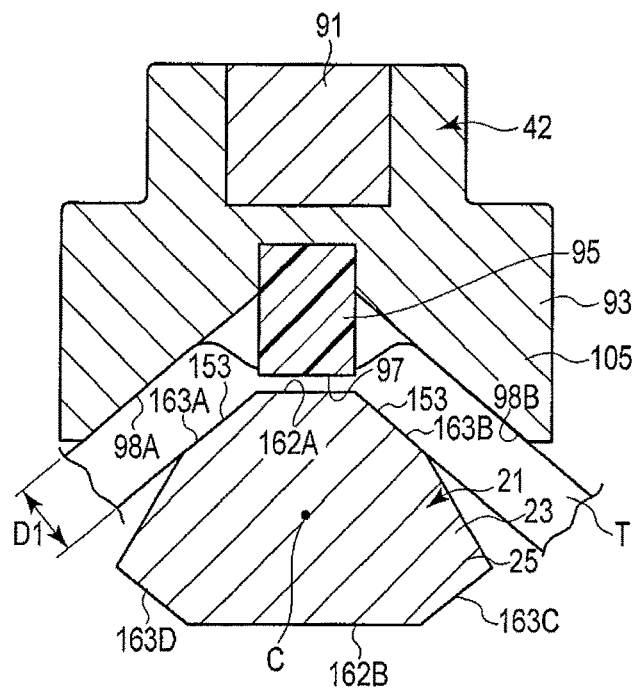
FIG. 31 is a schematic sectional view showing configurations of a distal portion of a probe unit and a jaw according to a modification of the third embodiment in the first treatment mode.
Figure 32:
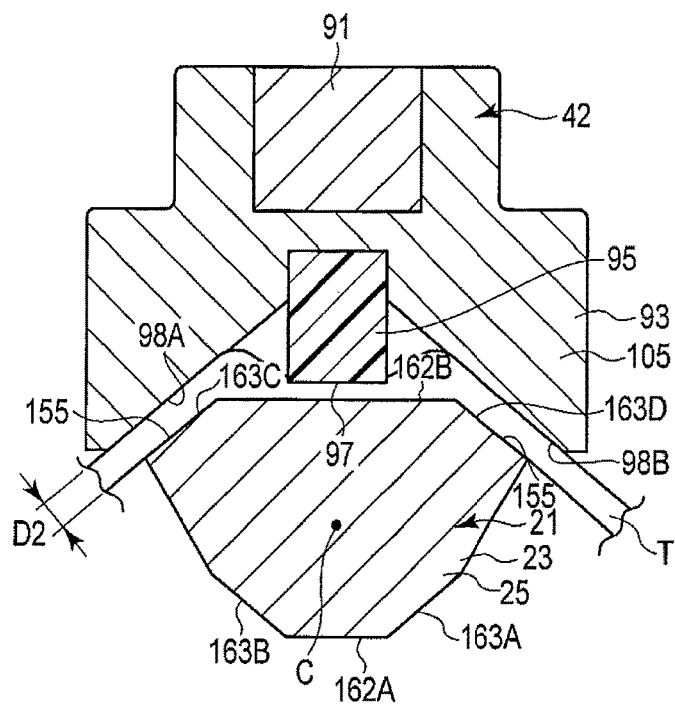
FIG. 32 is a schematic sectional view showing the configurations of the distal portion of the probe unit and the jaw according to the modification of the third embodiment in the second treatment mode.

According to the third embodiment, in the second treatment mode, the probe electric conducting portion 23 is located to be rotated relative to the jaw 42 and the sheath unit 5 by a rotation angle of about 90° in one of the directions around the longitudinal axis from the first treatment mode. However, the present invention is not limited to this. For example, as in a second modification shown in FIG. 31 and FIG. 32, in the second treatment mode, the probe electric conducting portion 23 is located to be rotated relative to the jaw 42 and the sheath unit 5 by a rotation angle of about 180° in one of the directions around the longitudinal axis from the first treatment mode.

In the present modification, the probe electric conducting portion 23 includes a first probe perpendicularly facing surface 162A which is parallel to the jaw perpendicularly facing surface 97 in the first treatment mode. In the first treatment mode, the jaw perpendicularly facing surface (abutting portion) 97 can abut on the first probe perpendicularly facing surface 162A. A first probe obliquely facing surface 163A and a second probe obliquely facing surface 163B are provided on both sides of the first probe perpendicularly facing surface 162A in width directions which are directions perpendicular to the longitudinal axis C and perpendicular to the opening-and-closing directions of the jaw 42. In the first treatment mode, the first probe obliquely facing surface 163A is substantially parallel to the jaw obliquely facing surface 98A, and faces the jaw obliquely facing surface 98A. The second probe obliquely facing surface 163B is substantially parallel to the jaw obliquely facing surface 98B, and faces the jaw obliquely facing surface 98B. That is, a first electrode facing surface 153 which faces the jaw electric conducting portion 93 in the first treatment mode is formed by the first probe obliquely facing surface 163A and the second probe obliquely facing surface 163B.

In the first treatment mode, the distance between the first electrode facing surface 153 (the first probe obliquely facing surface 163A and the second probe obliquely facing surface 163B) of the first electrode portion 25 and the jaw electric conducting portion 93 (the jaw obliquely facing surfaces 98A and 98B) of the second electrode portion 105 is the first distance D1. Therefore, the first electrode facing surface 153 faces the jaw electric conducting portion 93 with being spaced by the first distance D1.

The probe electric conducting portion 23 includes a second probe perpendicularly facing surface 162B which is parallel to the jaw perpendicularly facing surface 97 in the second treatment mode. The second probe perpendicularly facing surface 162B is located apart from the first probe perpendicularly facing surface 162A by an angular position of about 180° in one of the directions around the longitudinal axis. In the second treatment mode, the jaw perpendicularly facing surface (abutting portion) 97 can abut on the second probe perpendicularly facing surface 162B.

A third probe obliquely facing surface 163C and a fourth probe obliquely facing surface 163D are provided on both sides of the second probe perpendicularly facing surface 162B in width directions which are directions perpendicular to the longitudinal axis C and perpendicular to the opening-and-closing directions of the jaw 42. In the second treatment mode, the third probe obliquely facing surface 163C is substantially parallel to the jaw obliquely facing surface 98A, and faces the jaw obliquely facing surface 98A. The fourth probe obliquely facing surface 163D is substantially parallel to the jaw obliquely facing surface 98B, and faces the jaw obliquely facing surface 98B. That is, the second electrode facing surface 155 which faces the jaw electric conducting portion 93 in the second treatment mode is formed by the third probe obliquely facing surface 163C and the fourth probe obliquely facing surface 163D. The third probe obliquely facing surface 163C is located apart from the first probe obliquely facing surface 163A by an angular position of about 180° in one of the directions around the longitudinal axis. The fourth probe obliquely facing surface 163D is located apart from the second probe obliquely facing surface 163B by an angular position of about 180° in one of the directions around the longitudinal axis. The second electrode facing surface 155 is located apart from the first electrode facing surface 153 by an angular position of about 180° in one of the directions around the longitudinal axis.

In the second treatment mode, the distance between the second electrode facing surface 155 (the third probe obliquely facing surface 163C and the fourth probe obliquely facing surface 163D) of the first electrode portion 25 and the jaw electric conducting portion 93 (the jaw obliquely facing surfaces 98A and 98B) of the second electrode portion 105 is a second distance D2 smaller than the first distance D1. Therefore, the second electrode facing surface 155 faces the jaw electric conducting portion 93 at the second distance D2 smaller than the first distance D1.

As described above, according to the modification, the configuration which allows the distance between the first electrode portion 25 and the second electrode portion 105 to be smaller in the second treatment mode than in the first treatment mode is not limited to the third embodiment. That is, the probe electric conducting portion 23 has only to include the first electrode facing surface 153 which faces the jaw electric conducting portion 93 with being spaced by the first distance D1 from the jaw electric conducting portion 93 in the first treatment mode, and the second electrode facing surface 155 provided apart from the first electrode facing surface 153 in the directions around the longitudinal axis. In this case, the second electrode facing surface 155 faces the jaw electric conducting portion 93 with being spaced by the second distance D2 smaller than the first distance D1 from the jaw electric conducting portion 93 in the second treatment mode. The states of the sheath unit 5 and the probe unit 3 are switched by the rotation state switch portions (the rotation state switch levers 161A and 161B) between the relative rotation regulated state in which the sheath unit 5 and the probe unit 3 are unrotatable relative to each other in the directions around the longitudinal axis and the relative rotation allowed state in which the sheath unit 5 and the probe unit 3 are rotatable relative to each other in the directions around the longitudinal axis.

(Other Modifications)

Figure 33:
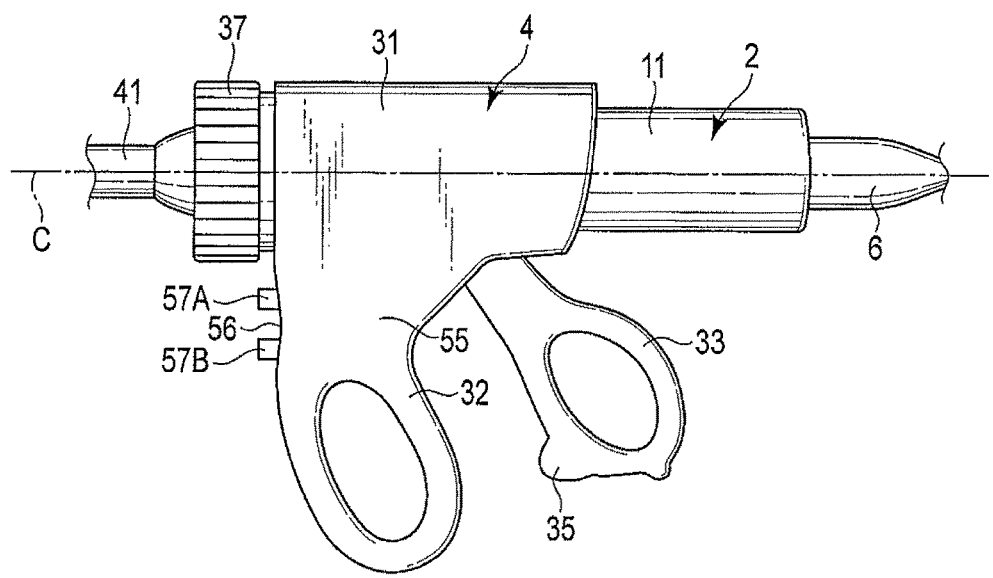
FIG. 33 is a schematic view showing a handle unit according to a modification of the first to third embodiments.

Although the movable handle 33 is located to the distal direction side of the fixed handle 32 in the first embodiment, the present invention is not limited to this. For example, as in a modification of the above-described embodiments shown in FIG. 33, the movable handle 33 may be located to the proximal direction side of the fixed handle 32. In the present modification, the movable handle 33 can open and close relative to the fixed handle 32 substantially parallel to the longitudinal axis C, as in the embodiments described above. In response to the open or close operation of the movable handle 33, the movable cylindrical member 46 of the sheath body 41 and the inner pipe 77 move relative to the handle unit 4 and the probe unit 3 along the longitudinal axis C. The jaw 42 is opened or closed relative to the probe electric conducting portion 23 by the movement of the inner pipe 77 along the longitudinal axis C.

According to the embodiments described above, in the first treatment mode, a high-frequency current is output from the high-frequency current supplier 9, and the high-frequency current is transmitted to the first electrode portion 25 and the second electrode portion 105. However, in the first treatment mode, for example, no high-frequency current may be output from the high-frequency current supplier 9, and no high-frequency current may be transmitted to the first electrode portion 25 and the second electrode portion 105. That is, in the first treatment mode, at least the ultrasonic vibration has only to be generated in the ultrasonic vibrator 12, and at least the ultrasonic vibration has only to be transmitted to the probe electric conducting portion 23. Consequently, a grasping target such as the living tissue T is cut and coagulated in the first treatment mode.

Thus, the first electrode portion 25 has only to be provided at least one of in a part between the jaw 42 and the probe electric conducting portion 23 in the opening-and-closing directions of the jaw 42 and in the probe electric conducting portion 23. In this case, the first electrode portion 25 has the first electric potential E1 when the high-frequency current is transmitted through the probe unit 3. Then the second electrode portion 105 has only to be provided at least one of in a part between the jaw 42 and the first electrode portion 25 in the opening-and-closing directions of the jaw 42 and in the jaw electric conducting portion 93. In this case, the second electrode portion 105 has the second electric potential E2 different in intensity from the first electric potential E1 when the high-frequency current is transmitted through the sheath unit 5. Then an inter-electrode distance changing unit has only to be configured to change the inter-electrode distance so that the second distance D2 between the first electrode portion 25 and the second electrode portion 105 in the second treatment mode in which a high-frequency current alone is transmitted to the first electrode portion 25 and the second electrode portion 105 is smaller than the first distance D1 between the first electrode portion 25 and the second electrode portion 105 in the first treatment mode in which at least the ultrasonic vibration is transmitted to the probe electric conducting portion 23. In the first embodiment described above, the inter-electrode distance changing unit includes the movement operation lever 83 which is the movement operation input portion. In the second embodiment, the inter-electrode distance changing unit includes the movement operation button 133 which is the movement operation input portion. In the third embodiment, the inter-electrode distance changing unit includes the rotation state switch levers 161A and 161B which are the rotation state switch portions and the rotational operation knob 37 which is the rotational operation input portion.

(Reference Example)

Now, a reference example of the present invention is described with reference to FIG. 34 to FIG. 36. The same parts as those in the first embodiment are provided with the same reference signs, and are not described.

FIG. 34 is a diagram showing the configurations of the distal portion of a probe unit 3 and a jaw 42. As shown in FIG. 34, in the present reference example, a probe electric conducting portion 23 is provided in the distal portion of a probe body 21 (a probe unit 3), as in the first embodiment. When a high-frequency current is transmitted through the probe unit 3, the probe electric conducting portion 23 functions as a first electrode portion 25 having a first electric potential E1.

As in the first embodiment, the jaw 42 is provided with a jaw body 91, a jaw electric conducting portion 93, and a pad member (insulating abutting member) 95. The jaw 42 also includes a first treatment region X1, and a second treatment region X2 provided to the proximal direction side of the first treatment region X1. That is, the second treatment region X2 is located apart from the first treatment region in one of the directions parallel to the longitudinal axis C. The treatment in the first treatment mode described above is conducted in the first treatment region X1. The treatment in the second treatment mode described above is conducted in the second treatment region X2.

FIG. 35 is a sectional view taken along the line 35-35 in FIG. 34. As shown in FIG. 35, the probe electric conducting portion 23 includes a probe perpendicularly facing surface 102, and probe obliquely facing surfaces 103A and 103B, as in the first embodiment. A first jaw perpendicularly facing surface (abutting portion) 171 is formed in the first treatment region X1 by the pad member 95. The first jaw perpendicularly facing surface 171 is perpendicular to the opening-and-closing directions of the jaw 42, and parallel to the probe perpendicularly facing surface 102. When the jaw 42 is closed relative to the probe electric conducting portion 23, the first jaw perpendicularly facing surface (abutting portion) 171 can abut on the probe perpendicularly facing surface 102 (the probe electric conducting portion 23).

Jaw obliquely facing surfaces 172A and 172B are formed by the jaw electric conducting portion 93 on both sides of the first jaw perpendicularly facing surface 171 in width directions which are directions perpendicular to the longitudinal axis C and perpendicular to the opening-and-closing directions of the jaw 42. The jaw obliquely facing surface 172A is substantially parallel to the probe obliquely facing surface 103A, and is provided apart from the probe obliquely facing surface 103B by the first distance D1. The jaw obliquely facing surface 172B is substantially parallel to the probe obliquely facing surface 103B, and is provided apart from the probe obliquely facing surface 103B by the first distance D1. Therefore, the first treatment region X1 has the first distance D1 between the probe electric conducting portion 23 (the probe obliquely facing surfaces 103A and 103B) of the first electrode portion 25 and the jaw electric conducting portion 93 (the jaw obliquely facing surfaces 172A and 172B) of the second electrode portion 105.

FIG. 36 is a sectional view taken along the line 36-36 in FIG. 34. As shown in FIG. 36, no pad member 95 is provided in the second treatment region X2. Jaw obliquely facing surfaces 172A and 172B are also formed in the second treatment region X2 by the jaw electric conducting portion 93. The positional relation of the jaw obliquely facing surfaces 172A and 172B with respect to the probe electric conducting portion 23 is similar to that in the first treatment region X1.

In the second treatment region X2, a second jaw perpendicularly facing surface 173 is formed by the jaw electric conducting portion 93. The jaw obliquely facing surfaces 172A and 172B are located on both sides of the second jaw perpendicularly facing surface 173 in width directions which are directions perpendicular to the longitudinal axis C and perpendicular to the opening-and-closing directions of the jaw 42. The second jaw perpendicularly facing surface 173 is perpendicular to the opening-and-closing directions of the jaw 42, and parallel to the probe perpendicularly facing surface 102. The second jaw perpendicularly facing surface 173 is located at the second distance D2 smaller than the first distance D1 from the probe perpendicularly facing surface 102. Therefore, the second treatment region X2 has the second distance D2 smaller than the first distance D1 between the probe electric conducting portion 23 (the probe perpendicularly facing surface 102) of the first electrode portion 25 and the jaw electric conducting portion 93 (the second jaw perpendicularly facing surface 173) of the second electrode portion 105.

The treatment in the first treatment mode described above is conducted so that a grasping target is grasped between the first treatment region X1 of the jaw 42 and the probe electric conducting portion 23. In the first treatment region X1, the first jaw perpendicularly facing surface 171 is formed by the pad member 95. Thus, the distance between the probe electric conducting portion 23 (the probe obliquely facing surfaces 103A and 103B) of the first electrode portion 25 and the jaw electric conducting portion 93 (the jaw obliquely facing surfaces 172A and 172B) of the second electrode portion 105 is the first distance D1. The first distance D1 is sufficiently great. Therefore, the contact between the first electrode portion 25 (the probe electric conducting portion 23) and the second electrode portion 105 (the jaw electric conducting portion 93) is effectively prevented even when the probe body 21 (the probe unit 3) is being ultrasonically vibrated. This effectively prevents the breakdown of the grasping treatment device 1 caused by a short circuit.

The probe body 21 is being ultrasonically vibrated in the first treatment mode. Thus, the pad member 95 which can abut on the probe electric conducting portion 23 while the jaw 42 is closed relative to the probe electric conducting portion 23 is worn by the treatment in the first treatment mode. As described above, the first distance D1 between the first electrode portion 25 and the second electrode portion 105 is greater in the first treatment region X1. Thus, even if the pad member 95 is worn by the treatment in the first treatment mode, a time distance from the start of the use of the grasping treatment device 1 to the contact between the probe electric conducting portion (the first electrode portion 25) and the jaw electric conducting portion 93 (the second electrode portion 105) is longer (prolonged). Therefore, the life of the grasping treatment device 1 is prolonged.

The treatment in the second treatment mode described above is conducted so that the grasping target is grasped between the second treatment region X2 of the jaw 42 and the probe electric conducting portion 23. In the second treatment region X2, no pad member 95 is provided, and the second jaw perpendicularly facing surface 173 is formed by the jaw electric conducting portion 93. Thus, the distance between the probe electric conducting portion 23 (the probe perpendicularly facing surface 102) of the first electrode portion 25 and the jaw electric conducting portion 93 (the second jaw perpendicularly facing surface 173) of the second electrode portion 105 is the second distance D2. The second distance D2 is smaller than the first distance D1. That is, the distance between the first electrode portion 25 and the second electrode portion 105 is smaller in the second treatment region X2 than in the first treatment region X1. Since the distance between the first electrode portion 25 and the second electrode portion 105 is smaller, the reformation of the living tissue T (grasping target) with the high-frequency current is more accelerated in the second treatment region X2 than in the first treatment region X1. Therefore, the performance of the coagulation of the grasping target with the high-frequency current is improved, so that the deterioration in the performance of the coagulation of the grasping target is prevented in the second treatment mode, which does not use the ultrasonic vibration. Consequently, the grasping target (living tissue) can be stably sealed by the treatment using the second treatment region X2 in the second treatment mode, which does not use the ultrasonic vibration.

In the second treatment region X2, the probe perpendicularly facing surface 102 of the probe electric conducting portion 23 is perpendicular to the opening-and-closing directions of the jaw 42. The second jaw perpendicularly facing surface 173 of the jaw electric conducting portion is parallel to the probe perpendicularly facing surface 102, and faces the probe perpendicularly facing surface 102. Since the probe perpendicularly facing surface 102 and the second jaw perpendicularly facing surface 173 are perpendicular to the opening-and-closing directions of the jaw 42, the grasping force to grasp the grasping target between the jaw electric conducting portion 93 (the second electrode portion 105) and the probe electric conducting portion 23 (the first electrode portion 25) is greater. The greater grasping force further improves the performance of the coagulation of the grasping target with the high-frequency current. Consequently, the grasping target (living tissue) is more stably sealed.

Other characteristic technical matters according to the present invention are additionally set forth below.

Notes (Additional Note 1)

A grasping treatment device comprising:

a probe unit which extends along a longitudinal axis, and which is configured to transmit an ultrasonic vibration from a proximal direction toward a distal direction;

a sheath unit through which the probe unit is inserted, and which is electrically insulated from the probe unit;

a probe electric conducting portion which is provided in a distal portion of the probe unit, and which functions as a first electrode portion having a first electric potential when a high-frequency current is transmitted thereto through the probe unit; and a jaw attached to a distal portion of the sheath body to be openable and closable relative to the probe electric conducting portion, the jaw including an abutting portion which is made of an insulating material, and which is abutable on the probe electric conducting portion when the jaw is closed relative to the probe electric conducting portion, and a jaw electric conducting portion which functions as a second electrode portion having a second electric potential different in intensity from the first electric potential when a high-frequency current is transmitted thereto through the sheath unit, wherein the jaw includes a first treatment region in which the abutting portion is provided, and in which the jaw electric conducting portion is spaced by a first distance from the probe electric conducting portion, a treatment in a first treatment mode in which at least the ultrasonic vibration is transmitted to the probe electric conducting portion being configured to be conducted in the first treatment region, a second treatment region in which the abutting portion is not provided, and in which the jaw electric conducting portion is spaced by a second distance smaller than the first distance from the probe electric conducting portion, the second treatment region being located apart from the first treatment region in directions parallel to the longitudinal axis, a treatment in a second treatment mode in which the high-frequency current alone is transmitted to the probe electric conducting portion and the jaw electric conducting portion being configured to be conducted in the second treatment region.

(Additional Note 2)

The grasping treatment device according to additional note 1, wherein the probe electric conducting portion includes a probe perpendicularly facing surface which is located perpendicularly to opening-and-closing directions of the jaw, and which faces the jaw, the abutting portion includes a first jaw perpendicularly facing surface which is abutable on the probe perpendicularly facing surface in the first treatment region, and which is parallel to the probe perpendicularly facing surface, and the jaw electric conducting portion includes a second jaw perpendicularly facing surface, the second jaw perpendicularly facing surface being parallel to the probe perpendicularly facing surface, and the second jaw perpendicularly facing surface being located to be spaced by the second distance from the probe perpendicularly facing surface in the second treatment region.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment device comprising:
    a probe body which is extended along a longitudinal axis and which is configured to transmit an ultrasonic vibration;
    a probe electric conducting portion which is provided to a distal portion of the probe body, the probe electric conducting portion having a first electric potential when a high-frequency current is transmitted thereto;

a jaw which is openable and closable relative to the probe body;

a jaw electric conducting portion which is provided in the jaw while facing the probe electric conducting portion, the jaw electric conducting portion having a second electric potential different in intensity from the first electric potential when the high-frequency current is transmitted thereto;

a first electrode facing surface which is provided on an outer surface of the probe electric conducting portion, a distance from the jaw electric conducting portion to the probe electric conducting portion being configured to be a first distance in a first state in which the first electrode facing surface faces the jaw electric conducting portion;

a second electrode facing surface which is provided to a different part from the first electrode facing surface on the outer surface of the probe electric conducting portion, the distance from the jaw electrode conducting portion to the probe electric conducting portion being configured to be a second distance smaller than the first distance in a second state in which the second electrode facing surface faces the jaw electric conducting portion; and an operation input portion configured to move the probe electric conducting portion relative to the jaw electric conducting portion so as to switch the probe electric conducting portion between the first state in which the first electrode facing surface faces the jaw electric conducting portion and the second state in which the second electrode facing surface faces the jaw electric conducting portion;

wherein the operation input portion is configured to switch the probe electric conducting portion to the first state during a first treatment mode in which at least the ultrasonic vibration is transmitted to the probe electric conducting portion, and configured to switch the probe electric conducting portion to the second state during a second treatment mode in which the high-frequency current alone is transmitted to the probe electric conducting portion and the jaw electric conducting portion.

2. The grasping treatment device according to claim 1, wherein the operation input portion is configured to rotate the probe electric conducting portion relative to the jaw electric conducting portion in one of a plurality of directions around the longitudinal axis so as to switch the probe electric conducting portion between the first state and the second state.

3. The grasping treatment device according to claim 1, further comprising:
a rotation state switch portion which is configured to switch a rotation state between a relative rotation regulated state in which the probe electric conducting portion and the jaw electric conducting portion are unrotatable relative to each other in the plurality of directions around the longitudinal axis and the relative rotation allowed state in which the probe electric conducting portion and the jaw electric conducting portion are rotatable relative to each other in the plurality of directions around the longitudinal axis.

4. The grasping treatment device according to claim 3, wherein the operation input portion is configured to input an operation of rotating the jaw and the probe body integrally in one of the plurality of directions around the longitudinal axis in the relative rotation regulated state.

5. The grasping treatment device according to claim 3, wherein the jaw and the probe body are configured to rotate relative to each other in one of the plurality of directions around the longitudinal axis in accordance with a switching by the operation input portion in the relative rotation allowed state.

6. The grasping treatment device according to claim 3, further comprising: a sheath body through which the probe body is inserted, the sheath body being electrically insulating from the probe body,
wherein the jaw is attached to the sheath body, and
the rotation state switch portion is configured to switch a coupling state of the sheath body with the probe body so as to switch the rotation state between the relative rotation regulated state and the relative rotation allowed state.

7. The grasping treatment device according to claim 1, wherein
the jaw includes an abutting portion which is made of an insulating material and which is abutable on the probe electric conducting portion, and
the jaw electric conducting portion is configured to form a clearance with respect to the probe electric conducting portion when the abutting portion is in abutment with the probe electric conducting portion.

\* \* \* \* \*